United States Patent [19]

Grossman et al.

[11] Patent Number: 5,514,543

[45] Date of Patent: *May 7, 1996

[54] METHOD AND PROBE COMPOSITION FOR DETECTING MULTIPLE SEQUENCES IN A SINGLE ASSAY

[75] Inventors: Paul D. Grossman, Burlingame; Steven Fung, Palo Alto; Steven M. Menchen, Fremont; Sam L. Woo, Redwood City; Emily S. Win-Deen, Foster City, all of Calif.

[73] Assignee: Applied Biosystems, Inc., Foster City, Calif.

[*] Notice: The term of this patent shall not extend beyond the expiration date of Pat. No. 5,470,705.

[21] Appl. No.: 102,372

[22] Filed: Aug. 4, 1993

Related U.S. Application Data

[63] Continuation-in-part of Ser. No. 973,118, Nov. 6, 1992, abandoned, which is a continuation-in-part of Ser. No. 866,018, Apr. 7, 1992, and Ser. No. 862,642, Apr. 3, 1992, abandoned.

[51] Int. Cl.⁶ .................................................. C12Q 1/68
[52] U.S. Cl. .......................... 435/6; 435/91.2; 435/91.52; 436/94
[58] Field of Search ................... 435/6, 91.2, 91.52; 536/24.3; 436/94

[56] References Cited

U.S. PATENT DOCUMENTS

| | | | |
|---|---|---|---|
| 4,683,202 | 7/1987 | Mullis | 435/91.2 |
| 4,925,785 | 5/1990 | Wang et al. | 435/6 |
| 5,011,769 | 4/1991 | Duck et al. | 435/6 |
| 5,108,568 | 4/1992 | Van Alstine | 204/180.1 |

FOREIGN PATENT DOCUMENTS

WO92/08728  5/1992  WIPO.

OTHER PUBLICATIONS

Grossman et al., *Nucleic Acids Res.* 22(21), 4527–4534 (1994).
Duck et al., *BioTechniques* 9(2), 142–147 (1990).
Karger et al., *Nucleic Acids Res.* 19(18), 4955–4962 (Sep. 1991).
Haralambidis et al., *Nucleic Acids Res.* 18(3), 493–499 (1990).
Agrawal, S., and J.-Y. Tang, "Site-specific functionalization of oligodeoxynucleotides for non–radioactive labelling," *Tetra–hedron Letters* 31(11): 1543–1546 (1990).
Barany, F., "Genetic disease detection and DNA amplification using cloned thermostable ligase," *Proc. Natl. Acad. Sci. USA* 88: 189–193 (1991).
Cload, S. T., and A. Schepartz, "Polyether Tetered Oligonucleotide Probes," *J. Am. Chem. Soc.* 113: 6324 (1991).
Cohen, A. S., et al., "High–Performance Capillary Electrophoretic Separation of Bases, Nucleosides, and Oligonucleotides: Retention Manipulation via Micellar Solutions and Metal Additives," *Anal. Chem.* 59(7): 1021–1027 (1987).
Connell, C., et al., "Automated DNA Sequence Analysis," *BioTechniques* 5(4): 342–348 (1987).
Jorgenson, J. W., and K. D. Lukacs, "Capillary zone Electrophoresis," *Science* 222: 266–272 (1983).
Kornher, J. S., and K. J. Livak, "Mutation detection using nucleotide analogs that alter electrophoretic mobility," *Nucleic Acids Research* 17(19): 7779–7784 (1989).
Muller, W., et al., "Polyethylene glycol derivatives of base and sequence specific DNA ligands: DNA interaction and application for base specific separation of DNA fragments by gel electrophoresis," *Nucleic Acids Research* 9(1): 95–119 (1981).
Noolandi, J., "A new concept for sequencing DNA by capillary electrophoresis," *Electrophoresis* 13: 394–395 (1992).
Skolnick, M. H., and R. B. Wallace, "Simultaneous Analysis of Multiple Polymorphic Loci Using Amplified Sequence Polymorphisms (ASPs)," *Genomics* 2: 273–279 (1988).
Winn–Deen, E. S., and D. M. Iovannesci, "Sensitive Fluorescence Method for Detecting DNA Ligation Amplification Products," *Clinical Chemistry* 37(9): 1522–1523 (1991).
Wu, D. Y., and R. B. Wallace, "The Ligation Amplification Reaction (LAR)–Amplification of Specific DNA Sequences Using Sequential Rounds of Template–Dependent Ligation," *Genomics* 4:560–569 (1989).
Wu, D. Y., and R. B. Wallace, "Specificity of the nick–closing activity of bacteriophage T4 DNA ligase," *Gene* 76: 245–254 (1988).
"Optimization and Troubleshooting DNA Sequencing with the Model 370A for use with Version 1.20 data analysis software," Applied Biosystems User Bulletin No. 7, pp. 1–15 (Apr. 15, 1988).

Primary Examiner—W. Gary Jones
Assistant Examiner—Kenneth R. Horlick
Attorney, Agent, or Firm—Peter J. Dehlinger; Vincent M. Powers

[57] ABSTRACT

Method and composition for detecting one or more selected polynucleotide regions in a target polynucleotide. In one embodiment of the invention, a plurality of different-sequence probe pairs are added to a target polynucleotide, where each probe pair includes two polynucleotide probe elements which are complementary in sequence to adjacent portions of a selected one of the target sequences in the target polynucleotide. In each probe pair, one of the probe elements contains a non-polynucleotide polymer chain which imparts a distinctive mobility to the associated probe pair, when the elements in the pair are ligated. The other element in the pair contains a detectable reporter label. After the probe pairs have been allowed to hybridize with the target polynucleotide, the hybridized polynucleotides are treated under conditions effective to ligate the end subunits of target-bound probe elements when their end subunits are base-paired with adjacent target bases. The ligated probe pairs are then released from the target polynucleotide and separated electrophoretically in a sieving matrix, or chromatographically.

46 Claims, 18 Drawing Sheets

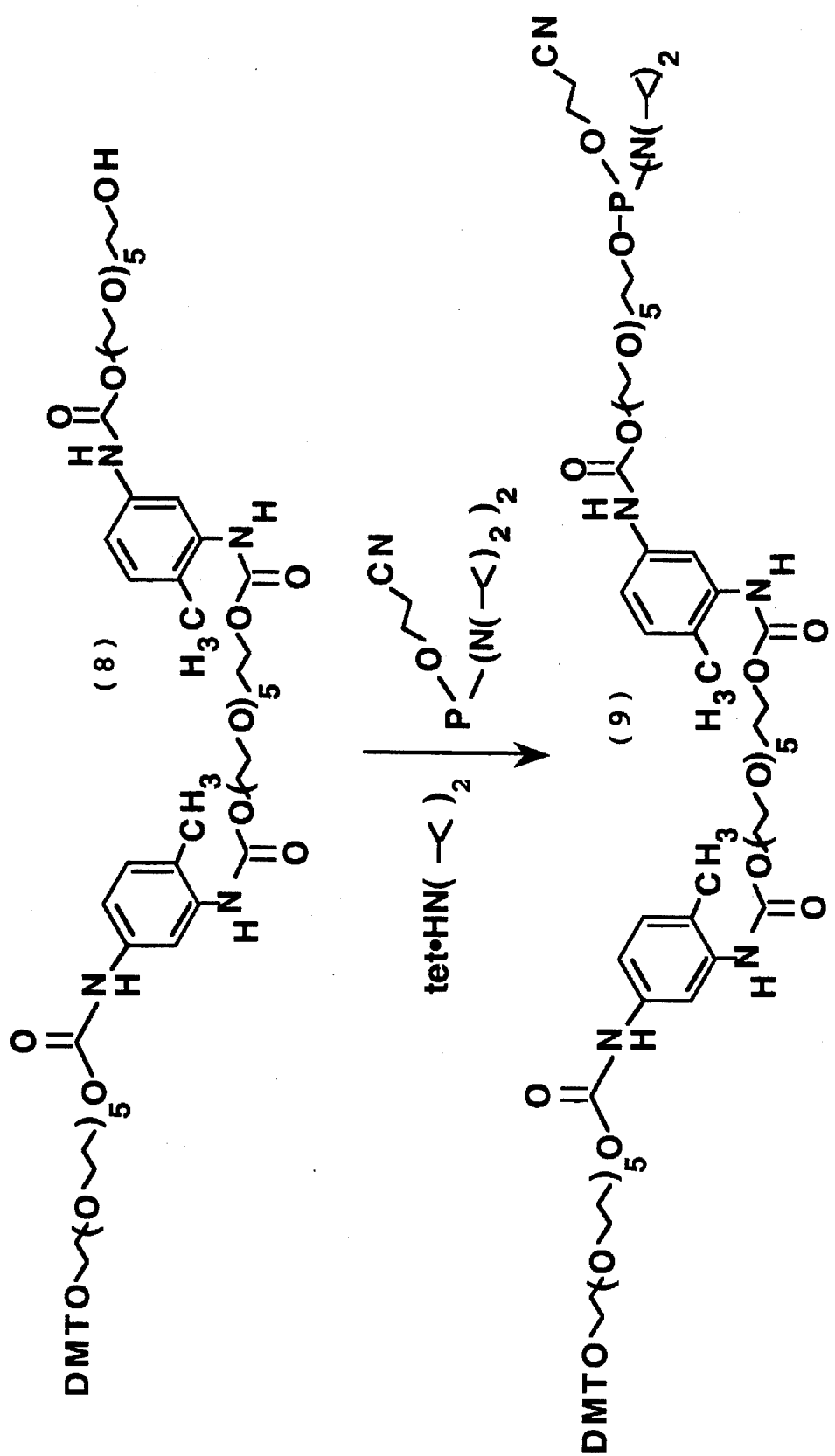
Fig. 3 (con't)

LIGATE

DENATURE, REANNEAL

LIGATE

DENATURE

REPEAT N-2 TIMES

× $2^N$

↓ POLYMERASE, LABELED dNTP

↓ Denature, reanneal

↓ Denature, reanneal

↓ RNAase H, DENATURE

↓ LIGATE, DENATURE

POLYMERASE/
EXONUCLEASE

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: synthetic polynucleotide/F508 region
            of cystic fibrosis gene ( x i ) SEQUENCE DESCRIPTION: SEQ ID NO:1:

GCACCATTAA AGAAAATATC ATCTTTGGTG TTTCCTATGA TGAATATA    48

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( C ) INDIVIDUAL ISOLATE: synthetic polynucleotide ( x i ) SEQUENCE DESCRIPTION: SEQ ID NO:2:

TTGGTGTTTC CTATGATGAA TATA    24

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

(i i i) HYPOTHETICAL: NO (i v) ANTI-SENSE: NO (v i) ORIGINAL SOURCE:
   (C) INDIVIDUAL ISOLATE: synthetic polynucleotide (x i) SEQUENCE DESCRIPTION: SEQ ID NO:3:

GGCACCATTA AAGAAAATAT CATCT    25

(2) INFORMATION FOR SEQ ID NO:4:

(i) SEQUENCE CHARACTERISTICS:
      (A) LENGTH: 4 amino acids
      (B) TYPE: amino acid
      (C) STRANDEDNESS: single
      (D) TOPOLOGY: linear (i i) MOLECULE TYPE: peptide (i i i) HYPOTHETICAL: NO (v i) ORIGINAL SOURCE:
      (C) INDIVIDUAL ISOLATE: synthetic tetrapeptide (x i) SEQUENCE DESCRIPTION: SEQ ID NO:4:

Phe  Ala  Phe  Ala
   1

(2) INFORMATION FOR SEQ ID NO:5:

(i) SEQUENCE CHARACTERISTICS:
      (A) LENGTH: 8 amino acids
      (B) TYPE: amino acid
      (C) STRANDEDNESS: single
      (D) TOPOLOGY: linear (i i) MOLECULE TYPE: peptide (i i i) HYPOTHETICAL: NO (v i) ORIGINAL SOURCE:
      (C) INDIVIDUAL ISOLATE: synthetic octapeptide (x i) SEQUENCE DESCRIPTION: SEQ ID NO:5:

Phe  Ala  Phe  Ala  Phe  Ala  Phe  Ala
   1                   5

(2) INFORMATION FOR SEQ ID NO:6:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
      (C) INDIVIDUAL ISOLATE: synthetic polynucleotide (x i) SEQUENCE DESCRIPTION: SEQ ID NO:6:

TTGGTGTTTC CTATGATGAA TATAG    25

(2) INFORMATION FOR SEQ ID NO:7:

(i) SEQUENCE CHARACTERISTICS:
      (A) LENGTH: 26 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthetic polynucleotide (xi) SEQUENCE DESCRIPTION: SEQ ID NO:7:

CTATATTCAT CATAGGAAAC ACCAAA                26

(2) INFORMATION FOR SEQ ID NO:8:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(C) INDIVIDUAL ISOLATE: synthetic polynucleotide (xi) SEQUENCE DESCRIPTION: SEQ ID NO:8:

GATGATATTT TCTTTAATGG TGCC                  24

METHOD AND PROBE COMPOSITION FOR DETECTING MULTIPLE SEQUENCES IN A SINGLE ASSAY

This application is a continuation-in-part of co-owned applications Ser. No. 08/973,118, filed Nov. 6, 1992, abandoned, which is a continuation-in-part of co-owned applications Ser. No. 07/866,018, filed Apr. 7, 1992 and Ser. No. 07/862,642, filed Apr. 3, 1992 abandoned.

FIELD OF THE INVENTION

The present invention relates to a probe composition and method for use in detecting selected sequences in a target polynucleotide.

REFERENCES

Agrawal, S., et al., (1990) Tetrahedron Letts. 31:1543–1546.

Applied Biosystems, DNA Sequencer User Bulletin, #11, "Synthesis of Fluorescent Dye-Labeled Oligonucleotides for Use as Primers in Fluorescence-Based DNA Sequencing (1989).

Blake, et al., Biochemistry, 24:6132 (1985a).

Blake, et al., Biochemistry, 24:6139 (1985b).

Caruthers et al., J. Am Chem Soc, 113(6324) (1991).

Cohen, A. S., et al., Anal Chem, 59(7):1021 (1987).

Cohen, A. S., et al., J. Chrom. 516:49 (1990).

Connell, C., et al., Biotechniques, 5:342 (1987).

Cload, S. T., et al., J Am Chem Soc, 113: 6324 (1991).

Froehler, et al., Nucleic Acids Res, 16:4831 (1988).

Grossman, P. G., and Colburn, J. C., Eds., *Capillary Electrophoresis*, Academic press, Inc., San Diego, Calif., 1992.

Hermans, J. J., J Polymer Sci, 18(257) (1953).

Kornberg, A., et al., "DNA Replication", pp 46–47, W.H. Freeman and Co., New York (1992).

Landegren, U., et al., Science, 241:1077 (1988).

Mathies, R. A., and Huang, X. C. Nature 359:167 (1992).

Miller, P. S., et al, Biochemistry, 18:5134 (1979).

Miller, P. S., et al., J Biol Chem, 255:6959 (1980).

Miller, P. S., et al., Bioconjugate Chem, 1 (187) (1990).

Mullis, K., U.S. Pat. No. 4,683,202 (1987).

Murakami, et al., Biochemistry, 24:4041 (1985).

Olivera, B. M., et al., Biopolymers, 2(245) (1964).

Saiki, R. K., et al., Science, 230:1350 (1985).

Stirchak, E. P., et al., Organic Chem, 52:4202 (1987).

Terabe, S., et al., Anal Chem, 57(4):834 (1985).

Towns, J. K., et al., Anal Chem, 63:1126 (1991).

Whiteley, N. M., et al., U.S. Pat. No. 4,883,750 (1989).

Winn-Deen, E., et al., Clin Chem, 37:1522 (1991).

Wu, D. Y., et al., Genomics, 4:560 (1989).

Zhu M. D., et al., U.S. Pat. No. 5,089,111 (1992).

BACKGROUND OF THE INVENTION

A variety of DNA hybridization techniques are available for detecting the presence of one or more selected polynucleotide sequences in a sample containing a large number of sequence regions. In a simple method, which relies on fragment capture and labeling, a fragment containing a selected sequence is captured by hybridization to an immobilized probe. The captured fragment can be labeled by hybridization to a second probe which contains a detectable reporter label.

Another widely used method is Southern blotting. In this method, a mixture of DNA fragments in a sample are fractionated by gel electrophoresis, then fixed on a nitrocellulose filter. By reacting the filter with one or more labeled probes under hybridization conditions, the presence of bands containing the probe sequence can be identified. The method is especially useful for identifying fragments in a restriction-enzyme DNA digest which contain a given probe sequence, and for analyzing restriction-fragment length polymorphisms (RFLPs).

Another approach to detecting the presence of a given sequence or sequences in a polynucleotide sample involves selective amplification of the sequence(s) by polymerase chain reaction (Mullis, Saiki). In this method, primers complementary to opposite end portions of the selected sequence(s) are used to promote, in conjunction with thermal cycling, successive rounds of primer-initiated replication. The amplified sequence may be readily identified by a variety of techniques. This approach is particularly useful for detecting the presence of low-copy sequences in a polynucleotide-containing sample, e.g., for detecting pathogen sequences in a body-fluid sample.

More recently, methods of identifying known target sequences by probe ligation methods have been reported (Wu, Whiteley, Landegren, Winn-Deen). In one approach, known as oligonucleotide ligation assay (OLA), two probes or probe elements which span a target region of interest are hybridized with the target region. Where the probe elements match (basepair with) adjacent target bases at the confronting ends of the probe elements, the two elements can be joined by ligation, e.g., by treatment with ligase. The ligated probe element is then assayed, evidencing the presence of the target sequence.

In a modification of this approach, the ligated probe elements act as a template for a pair of complementary probe elements. With continued cycles of denaturation, reannealing and ligation in the presence of the two complementary pairs of probe elements, the target sequence is amplified geometrically, allowing very small amounts of target sequence to be detected and/or amplified. This approach is also referred to as Ligase Chain Reaction (LCR).

There is a growing need, e.g., in the field of genetic screening, for methods useful in detecting the presence or absence of each of a large number of sequences in a target polynucleotide. For example, as many as 200 different mutations have been associated with cystic fibrosis. In screening for genetic predisposition to this disease, it is optimal to test all of the possible different gene sequence mutations in the subject's genomic DNA, in order to make a positive identification of a "cystic fibrosis". Ideally, one would like to test for the presence or absence of all of the possible mutation sites in a single assay.

These prior-art methods described above are not readily adaptable for use in detecting multiple selected sequences in a convenient, automated single-assay format. It is therefore desirable to provide a rapid, single-assay format for detecting the presence or absence of multiple selected sequences in a polynucleotide sample.

SUMMARY OF THE INVENTION

The present invention includes, in a first general embodiment, a method of detecting the presence or absence of a plurality of selected target sequences in a target polynucleotide. In practicing the method, a plurality of different-sequence probe pairs are added to a target polynucleotide, where each probe pair includes two polynucleotide probe elements which are complementary in sequence to adjacent portions of a selected one of the target sequences in the target polynucleotide. In each probe pair, one of the probe elements contains a polymer chain which imparts a distinctive electrophoretic mobility in a sieving matrix, to the associated probe pair, when the elements in the pair are ligated. In one embodiment, the polymer chains are non-polynucleotide chains. The other element in the pair contains a detectable reporter label.

After the probe pairs have been allowed to hybridize with the target polynucleotide, the hybridized polynucleotides are treated under conditions effective to ligate the end subunits of target-bound probe elements when their end subunits are base-paired with adjacent target bases. The ligated probe pairs are then released from the target polynucleotide and separated by electrophoresis in a sieving matrix.

In one embodiment, the polynucleotide portions of all of the probe pairs, in ligated form, are substantially the same in length. In this embodiment, separability of the ligated probe pairs relies predominantly on the non-polynucleotide polymers attached to each probe.

In a second embodiment, the ligated probe(s) are amplified by repeated cycles of probe binding and ligation. The ligated probe(s) may be amplified linearly by repeated binding and ligation of unligated probe to the target sequence. Alternatively, the ligated probe(s) may be amplified exponentially, by repeated cycles of probe binding and ligation in the presence of a second pair of first and second probe oligonucleotides which, together, make up a sequence that is complementary to the selected ligated probe.

In another embodiment, the second probe element in each probe includes two alternative-sequence oligonucleotides which (i) are complementary to alternative sequences in the same portion of an associated target sequence and (ii) are derivatized with different detectable reporters. This method allows the mutation state of the target sequence to be determined according to (a) a signature electrophoretic migration rate of each probe, which identifies the target sequence associated with that probe, and (b) a signature reporter label, which identifies the mutation state of that target sequence.

In another embodiment, one of the elements (e.g., the first-mentioned element) in each probe includes two alternative-sequence oligonucleotides which (i) are complementary to alternative sequences in the same portion of an associated target sequence and (ii) are derivatized with different polymer chains which impart a distinctive mobility to each associated probe pair, when the elements in the pair are ligated. This method allows the mutation state of the target sequence to be determined according to (a) a signature reporter label which identifies the target sequence associated with the associated probe, and (b) a signature mobility, which identifies the mutation state of the associated target sequence.

The polymer chain used in the method may be a substantially uncharged, water-soluble chain, such as a chain composed of polyethylene oxide (PEO) units or a polypeptide chain, where the chains attached to different-sequence binding polymers have different numbers of polymer units. Also included are polymers composed of units of multiple subunits linked by charged or uncharged linking groups.

In another embodiment, hybridization of the probes to the target polynucleotide is carried out with the target polynucleotide immobilized on a solid support. Following hybridization of the probes to the immobilized target polynucleotide, the target polynucleotide is washed to remove probe pairs not bound to the target polynucleotide in a sequence-specific manner. The target polynucleotide is then denatured to release probes bound in a sequence-specific manner.

In a second general embodiment, the invention includes a method of detecting the presence or absence of a plurality of selected target sequences in a target polynucleotide using chromatographic methods. In the method, a plurality of different-sequence probe pairs are added to a target polynucleotide, where each probe pair includes two polynucleotide probe elements which are complementary in sequence to adjacent portions of a selected one of the target sequences in the target polynucleotide. In each probe pair, one of the probe elements contains a polymer chain which imparts a distinctive elution characteristic in a chromatographic separation medium to the associated probe pair, when the elements in the pair are ligated. In one embodiment, the polymer chains are nonpolynucleotide chains. The other element in the pair contains a detectable reporter label.

After the probe pairs have been allowed to hybridize with the target polynucleotide, the hybridized polynucleotides are treated under conditions effective to ligate the end subunits of target-bound probe elements when their end subunits are base-paired with adjacent target bases. The ligated probe pairs are then released from the target polynucleotide and separated by chromatography.

The method can take the form of a variety of embodiments, including embodiments analogous to those described above for the first general embodiment.

In a more general aspect, a invention includes a method of distinguishing different-sequence polynucleotides electrophoretically in a non-sieving medium. In practicing the method, there are formed one or more different-sequence polynucleotide(s) which contain (i) a detectable reporter label and (ii) an attached polymer chain which imparts to each different-sequence polynucleotide, a distinctive electrophoretic mobility in a sieving matrix, or alternatively, for chromatographic separation, a distinctive elution characteristic in a chromatographic separation medium. The different-sequence polynucleotides which are formed are fractionated according to their mobilities and detected according to their observed mobilities and/or signature reporter labels. The method may take the form of various embodiments described hereinbelow.

Also forming part of the invention is a probe composition for use in detecting one or more of a plurality of different sequences in a target polynucleotide. The composition includes a plurality of sequence-specific probes, each characterized by (a) a binding polymer having a probe-specific sequence of subunits designed for base-specific binding of the polymer to one of the target sequences, under selected binding conditions, and (b) attached to the binding polymer, a polymer chain which imparts a distinctive electrophoretic mobility in a sieving matrix, or alternatively, for chromatographic separation, a distinctive elution characteristic in a chromatographic separation medium.

These and other objects and features of the invention will become more fully apparent when the following detailed description of the invention is read in conjunction with the accompanying drawings.

DETAILED DESCRIPTION OF THE INVENTION

I. Definitions

Figure 1A:
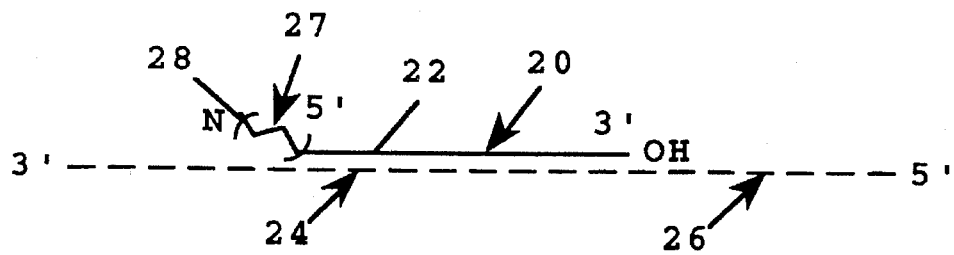
FIGS. 1A–1D illustrate three general types of probes and probe elements used in practicing various embodiments of the method of the invention.

"A target polynucleotide" may include one or more nucleic acid molecules, including linear or circularized single-stranded or double-stranded RNA or DNA molecules.

"Target nucleic acid sequence" means a contiguous sequence of nucleotides in the target polynucleotide. A "plurality" of such sequences includes two or more nucleic acid sequences differing in base sequence at one or more nucleotide positions.

"Sequence-specific binding polymer" means a polymer effective to bind to one target nucleic acid or sequence subset with base-sequence specificity, and which has a substantially lower binding affinity, under selected hybridization conditions, to any other target sequence or sequence subset in a given plurality of sequences in the test sample.

"Mobile phase" refers to the solvent phase used to elute analyte(s) from a chromatographic separation medium.

"A chromatographic separation medium" refers to a stationary or particulate phase which is effective to bind (i.e., adsorb) an analyte under selected mobile phase conditions, and to release the analyte under other selected mobile phase conditions; the quoted term also includes a separation medium such as employed in micellar electrokinetic capillary chromatography (e.g., Grossman et al., 1992, pp. 159–187).

"Capillary electrophoresis" means electrophoresis in a capillary tube or in a capillary plate, where the diameter of the separation column or thickness of the separation plate is between about 25–500 microns, allowing efficient heat dissipation throughout the separation medium, with consequently low thermal convection within the medium.

A "sieving matrix" or "sieving medium" means an electrophoresis medium that contains crosslinked or non-crosslinked polymers which are effective to retard electrophoretic migration of charged species through the matrix.

A "distinctive elution characteristic" of an analyte (e.g., a probe) is evidenced by (i) a distinctive, i.e., unique, migration rate in a chromatographic separation medium under selected isocratic or shallow gradient mobile phase conditions; (ii) a unique concentration threshold in a mobile phase gradient which, when exceeded, allows analyte to be eluted from the separation medium; or (iii) a unique elution time in a selected mobile phase gradient protocol.

A "distinctive electrophoretic mobility" of an analyte (e.g., a probe) is evidenced by a distinctive, i.e., unique, electrophoretic mobility of the analyte in a sieving matrix.

As used herein, a "distinctive mobility" refers generally to a "distinctive elution characteristic in a chromatographic separation medium" and/or a "distinctive electrophoretic mobility", as defined above.

A "labeled probe" refers to a probe which is composed of (i) a binding polymer effective to bind in a sequence-specific manner to a selected target sequence, (ii) a polymer chain which imparts to the binding polymer, a distinctive mobility in a chromatographic or electrophoretic separation, and (iii) a detectable reporter or tag.

A "reporter", "label", "reporter label", or "tag" refers to a fluorophore, chromophore, radioisotope, chemiluminescent, or spin label which allows direct detection of a labeled probe by a suitable detector, or a ligand, such as an antigen, or biotin, which can bind specifically and with high affinity to a detectable anti-ligand, such as a reporter-labeled antibody or avidin.

As used herein, the term "spectrally resolvable" in reference to a plurality of reporter labels means that the fluorescent emission bands of the dyes are sufficiently distinct, i.e. sufficiently non-overlapping, that target substances to which the respective dyes are attached, e.g. polynucleotides, can be distinguished on the basis of the fluorescent signal generated by the respective dyes by standard photodetection systems, e.g. employing a system of band pass filters and photomultiplier tubes, or the like, as exemplified by the systems described in U.S. Pat. Nos. 4,230,558, 4,811,218, or the like, or in Wheeless et al, pgs. 21–76, in Flow Cytometry: Instrumentation and Data Analysis (Academic Press, New York, 1985).

II. Probe Composition

This section describes several embodiments of probes designed for use in the present invention. In the typical case, the probe is part of a probe composition which contains a plurality of probes used for detecting one or more of a plurality of target sequences, according to methods described in Section III. The probes described with reference to FIGS. 1B and 1C are representative of probes or probe elements which make up probe compositions in accordance with the present invention.

A. Probe Structure

Figure 1B:
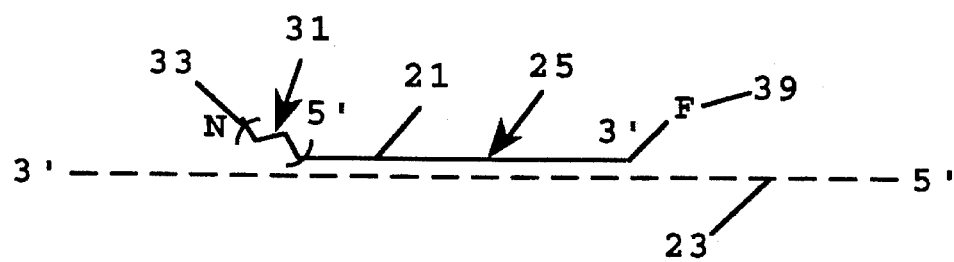
Figure 1C:
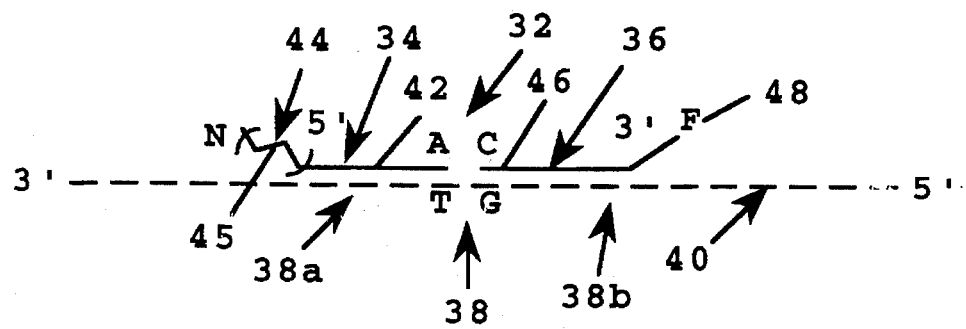

FIG. 1A shows a probe 20 which is one of a plurality of probes used in one embodiment of the method of the invention. As will be seen below, a probe composition containing a probe like probe 20 is designed for use in a "probe-extension" method of identifying target sequences, such as the sequence in region 24 of a target polynucleotide, indicated by dashed line at 26 in FIG. 1A, or in a "probe-capture" method for identifying such target sequences. These methods are discussed in Section IV below.

Probe 20 includes an oligonucleotide binding polymer 22 which preferably includes at least 10–20 bases, for requisite basepair specificity, and has a base sequence which is complementary to region 24 in target polynucleotide 26, with such in single-stranded form. Other probes in the composition have sequence specificities for other target regions of known sequence in the target polynucleotide. In a preferred embodiment, the binding polymers of the different-sequence probes all have substantially the same length, allowing hybridization of the different probes to the target polynucleotide with substantially the same hybridization reaction kinetics and thermodynamics ($T_m$).

Other binding polymers which are analogs of polynucleotides, such as deoxynucleotides with thiophosphodiester linkages, and which are capable of base-specific binding to single-stranded or double-stranded target polynucleotides are also contemplated. Polynucleotide analogs containing uncharged, but stereoisomeric methylphosphonate linkages between the deoxyribonucleoside subunits have been reported (Miller, 1979, 1980, 1990, Murakami, Blake, 1985a, 1985b). A variety of analogous uncharged phosphoramidate-linked oligonucleotide analogs have also been reported (Froehler). Also, deoxyribonucleoside analogs having achiral and uncharged intersubunit linkages (Stirchak) and uncharged morpholino-based polymers having achiral intersubunit linkages have been reported (U.S. Pat. No. 5,034,506). Such binding polymers may be designed for sequence specific binding to a single-stranded target molecule through Watson-Crick base pairing, or sequence-specific binding to a double-stranded target polynucleotide through Hoogstein binding sites in the major groove of duplex nucleic acid (Kornberg).

The oligonucleotide binding polymer in probe 20 is derivatized, at its 5' end, with a polymer 27 composed of N subunits 28. The units may be the subunits of the polymer or may be groups of subunits.

According to an important feature of the invention, each polymer chain (or elements forming a polymer chain) imparts to the corresponding binding polymer to which it is attached, a distinctive mobility under chromatographic or electrophoretic conditions as set forth in Section I above and described further below. As will be discussed below, the distinctive mobility can be achieved by differences in the number of units in the polymer chain.

Generally, the polymers forming the polymer chain may be homopolymers, random copolymers, or block copolymers, and the polymer is preferably in a linear configuration. Alternatively, the polymer chains may be in comb, branched, or dendritic configurations. In addition, although the invention is described herein with respect to a single polymer chain attached to an associated binding polymer at a single point, the invention also contemplates binding polymers which are derivatized by more than one polymer chain element, where the elements collectively form the polymer chain.

Preferred polymers are those which ensure that the probe is soluble in an aqueous medium. The polymers should also not affect the hybridization reaction. Where the binding polymers are highly charged, as in the case of oligonucleotides, the polymer chains are preferably uncharged.

Exemplary polymer chains may be formed using monomers (for example, polyethylene oxide or polypeptide units) that can differ in length by one or more backbone atoms. Such monomers can be linked directly to each other, or alternatively, by intervening linking groups which may be charged or uncharged.

In another embodiment the polymers can be dendritic polymers, such as polymers containing polyamidoamine branched polymers (Polysciences, Inc., Warrington, Pa.), for example.

Methods of synthesizing selected-length polymer chains, either separately or as part of a single-probe solid-phase synthetic method, are described below.

Figure 2:
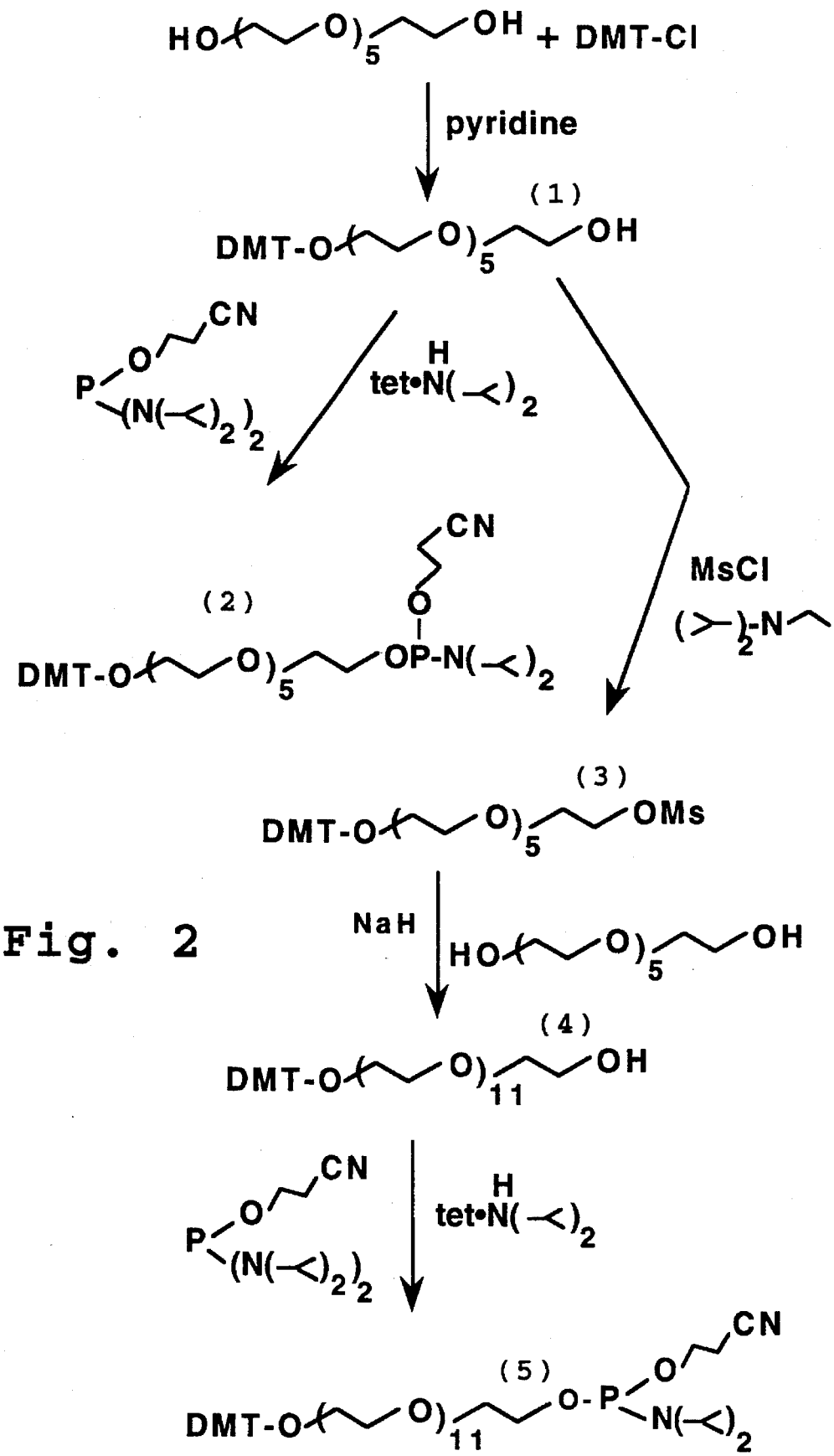
FIG. 2 illustrates methods of synthesis of polyethylene oxide polymer chains having a selected number of hexaethylene oxide (HEO) units.

In one preferred embodiment, the polymer chain is formed from polyethylene oxide units, where the HEO units are joined end-to-end to form an unbroken chain of ethylene oxide subunits, as illustrated in FIG. 2, or are joined by uncharged (FIG. 3) or charged (FIG. 5) linkages, as described below. Linkage of heptaethylene oxide units via amide linking groups is illustrated in FIG. 6, and polymer chains composed of short amino acid peptides are described in Example 7.

B. Probe Compositions

This section describes three additional probes or probe-element pairs which are useful in specific embodiments of the method of the invention and which themselves, either as single probes or as probe sets, form compositions in accordance with the invention.

FIG. 1B illustrates a probe 25 which has a sequence-specific oligonucleotide binding polymer 21 designed for sequence-specific binding to a region of a single-stranded target polynucleotide 23. By this is meant that the binding polymer contains a sequence of subunits effective to form a stable duplex or triplex hybrid with the selected single-stranded or double-stranded target sequence, respectively, under defined hybridization conditions. As will be seen with reference to FIG. 16 below, the binding polymer may contain both DNA and RNA segments. Attached to the binding polymer, at its 5' end, is a polymer chain 31 composed of N units 33, which imparts to the binding polymer a distinctive mobility, as described above. The 3' end of the binding polymer is derivatized with a reporter or tag 39. In one aspect, the invention includes a composition having a plurality of such probes, each with a different-sequence binding polymer targeted against different target regions of interest, and each having a distinctive mobility imparted by the associated polymer chain.

FIG. 1C illustrates a probe 32 which consists of first and second probe elements 34, 36, is designed particularly for detecting selected sequences in each of one or more regions, such as region 38, of a target polynucleotide, indicated by dashed line 40.

In the embodiment illustrated, the sequences of interest may involve mutations, for example, point mutations, or addition or deletion type mutations involving one or a small number of bases. In a typical example, the expected site of mutation is near the midpoint of the known-sequence target region, and divides that region into two subregions. In the example shown, the mutation is a point mutation, and the expected site of the mutation is at one of the two adjacent bases T-G, with the T base defining the 5' end of a subregion 38a, and the adjacent G base, defining the 3' end of adjacent subregion 38b. As will be seen below, the probe elements are also useful for detecting a variety of other types of target sequences, e.g., sequences related to pathogens or specific genomic gene sequences.

Probe element 32, which is representative of the first probe elements in the probe composition, is composed of an oligonucleotide binding polymer element 42 which preferably includes at least 10–20 bases, for requisite basepair specificity, and has a base sequence which is complementary to a subregion 38a in the target polynucleotide. In particular, the 3' end nucleotide bases are selected for base pairing to the 5' end nucleotide bases of the corresponding subregion, e.g., the A:T matching indicated. The oligonucleotide in the first probe element is derivatized, at its 5' end, with a polymer chain 44 composed of N preferably repeating units 45, substantially as described with respect to chain 27 formed from units 28. As described with respect to probe 20, the polymer chain in the first probe element imparts a mobility, under electrophoresis or chromatographic conditions, which is distinctive for each sequence-specific probe element in the composition.

Second probe element 36, which is also representative of the second probe elements in the probe composition, is composed of an oligonucleotide polymer binding element 46 which preferably includes at least 10–20 bases, for requisite basepair specificity, and has a base sequence which is complementary to a subregion 38b in the target polynucleotide. In particular, the 5' end nucleotide bases are selected for base pairing to the 3' end nucleotide bases of the corresponding subregion, e.g., the C:G matching indicated.

As seen in FIG. 1C, when the two probe elements are both hybridized to their associated target regions, the confronting end subunits in the two probes, in this example the confronting A and C bases, are matched with adjacent bases, e.g., the adjacent T and G bases in the target polynucleotide. In this condition, the two probe elements may be ligated at their confronting ends, in accordance with one embodiment of the invention described below, forming a ligated probe which contains both oligonucleotide elements, and has the sequence-specific polymer chain and a reporter attached at opposite ends of the joined oligonucleotides. It will be recognized that the condition of abutting bases in the two probes can also be produced, after hybridization of the probes to a target region, by removing overlapping deoxyribonucleotides by exonuclease treatment.

The second probe element is preferably labeled, for example, at its 3' end, with detectable reporter, such as reporter F indicated at 48 in FIG. 1C. Preferably the reporter is an optical reporter, such as a fluorescent molecule which can be readily detected by an optical detection system. A number of standard fluorescent labels, such as FAM, JOE, TAMRA, and ROX, which can be detected at different excitation wavelengths, and methods of reporter attachment to oligonucleotides, have been reported (Applied Biosystems, Connell).

In one embodiment, each probe includes two second probe elements, one element having an end-subunit base sequence which can basepair with a wildtype base in the target sequence, and a second element having an end-subunit base sequence which can basepair with an expected mutation in the sequence. The two alternative elements are labeled with distinguishable reporters, allowing for positive identification of wildtype or mutation sequences in each target region, as will be described in Section III below. Alternatively, the two second probe elements (e.g., oligonucleotides) may have the same reporters, and the first probe elements have polymer chains which impart to the two second probe elements, distinctive mobilities.

Figure 1D:
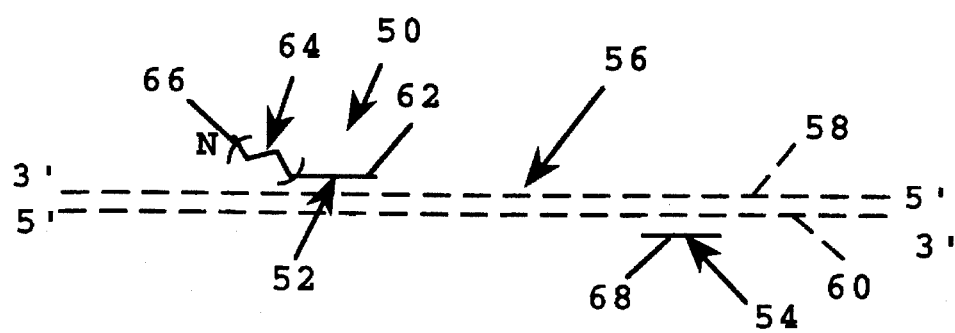

FIG. 1D shows a probe 50 which is representative of probes in a composition designed for use in another embodiment of the method of the invention. The probe, which consists of first and second primer elements 52, 54, is designed particularly for detecting the presence or absence of regions in a double-stranded target polynucleotide which are bounded by the primer-element sequences. In the example shown in FIG. 1D, the region bounded by the primer sequence is indicated at 56, and the two strands of a double-stranded target polynucleotide, by the dashed lines 58, 60.

Primer element 52, which is representative of the first primer elements in the probe composition, is composed of an oligonucleotide primer element 62 which preferably includes at least 7–15 bases, for requisite basepair specificity, and has a base sequence which is complementary to a 3'-end portion of region 56 in one of the two target strands, in this case, strand 58.

The oligonucleotide primer is derivatized, at its 5' end, with a polymer chain 64 composed of N preferably repeating units 66, substantially as described with respect to chain 27 formed from units 28. As described with respect to probe 20, the polymer chain in the first probe element imparts a mobility which is distinctive for each sequence-specific primer element in the composition.

Second primer element 54, which is also representative of the second probe elements in the probe composition, is composed of an oligonucleotide primer element 68 which also preferably includes at least 7–15 bases, for requisite basepair specificity, and has a base sequence which is complementary to a 5' end portion of the opposite strand—in this case, strand 60, of the duplex DNA forming region 56. The second primer element may be labeled with a detectable reporter, as described above. Alternatively, labeling can occur after formation of amplified target sequences, as described below.

C. Probe Preparation

Methods of preparing polymer chains in the probes generally follow known polymer subunit synthesis methods. Methods of forming selected-length polyethylene oxide-containing chains are discussed below, and detailed in Examples 1–5. It can be appreciated that these methods, which involve coupling of defined-size, multi-subunit polymer units to one another, directly or via linking groups, are applicable to a wide variety of polymers, such as polyethers (e.g., polyethylene oxide and polypropylene oxide), polyesters (e.g., polyglycolic acid, polylactic acid), polypeptides, oligosaccharides, polyurethanes, polyamides, polysulfonamides, polysulfoxides, polyphosphonates, and block copolymers thereof, including polymers composed of units of multiple subunits linked by charged or uncharged linking groups.

In addition to homopolymers, the polymer chains used in accordance with the invention include selected-length copolymers, e.g., copolymers of polyethylene oxide units alternating with polypropylene units. As another example, polypeptides of selected lengths and amino acid composition (i.e., containing naturally occurring or man-made amino acid residues), as homopolymers or mixed polymers, can be prepared, as described in Examples 5 and 7.

FIG. 2 illustrates one method for preparing PEO chains having a selected number of HEO units. As shown in the figure, HEO is protected at one end with dimethoxytrityl (DMT), and activated at its other end with methane sulfonate. The activated HEO can then react with a second DMT-protected HEO group to form a DMT-protected HEO dimer. This unit-addition is carried out successively until a desired PEO chain length is achieved. Details of the method are given in Example 1.

Example 2 describes the sequential coupling of HEO units through uncharged bisurethane tolyl groups. Briefly, with respect to FIG. 3, HEO is reacted with 2 units of tolylene-2,4-diisocyanate under mild conditions, and the activated HEO is then coupled at both ends with HEO to form a bisurethane tolyl-linked trimer of HEO.

Figure 4A:
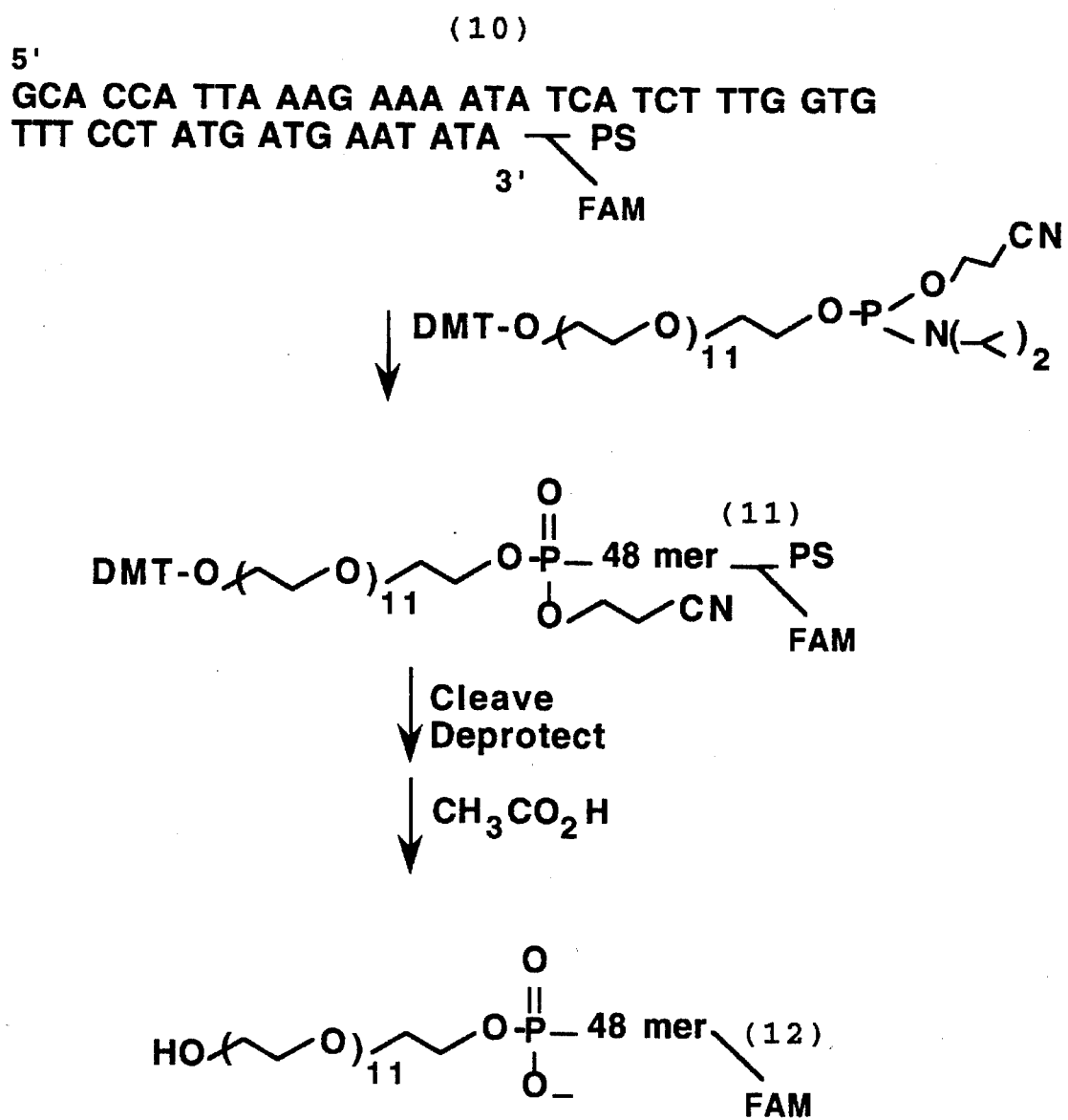
FIGS. 4A and 4B illustrate coupling reactions for coupling the polymer chains of FIGS. 2 and 3 to the 5' end of a polynucleotide, respectively.
Figure 4B:
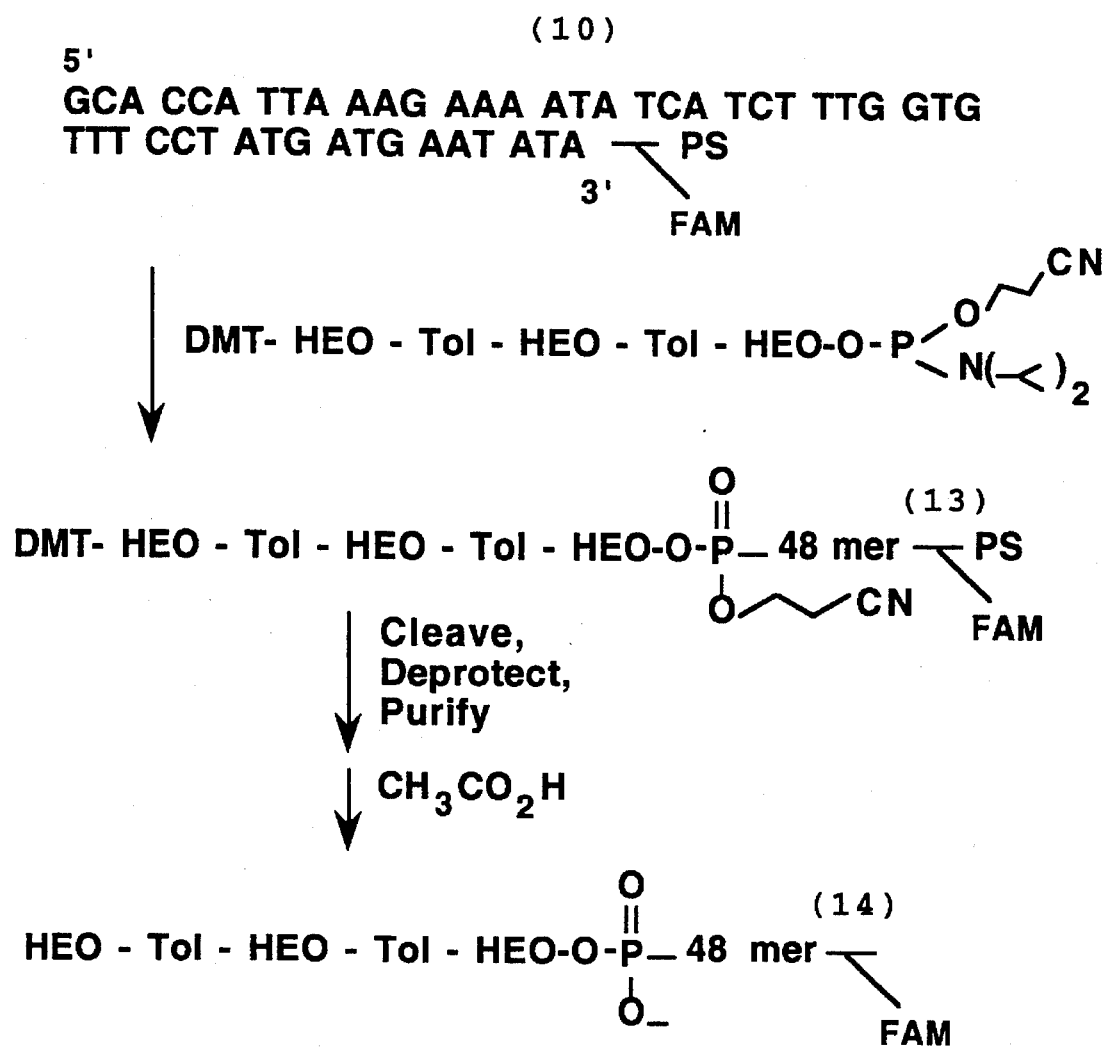

Coupling of the polymer chains to an oligonucleotide can be carried out by an extension of conventional phosphoramidite oligonucleotide synthesis methods, or by other standard coupling methods. FIG. 4A illustrates a procedure for coupling a PEO polymer chain to the 5' end of an oligonucleotide formed on a solid support, via phosphoramidite coupling. FIG. 4B illustrates the coupling of the above bisurethane tolyl-linked polymer chain to an oligonucleotide on a solid support, also via phosphoramidite coupling. Details of the two coupling methods are given in Examples 3B and 3C, respectively.

Alternatively, the polymer chain can be built up on an oligonucleotide (or other sequence-specific binding polymer) by stepwise addition of polymer-chain units to the oligonucleotide, using standard solid-phase synthesis methods.

Figure 5:
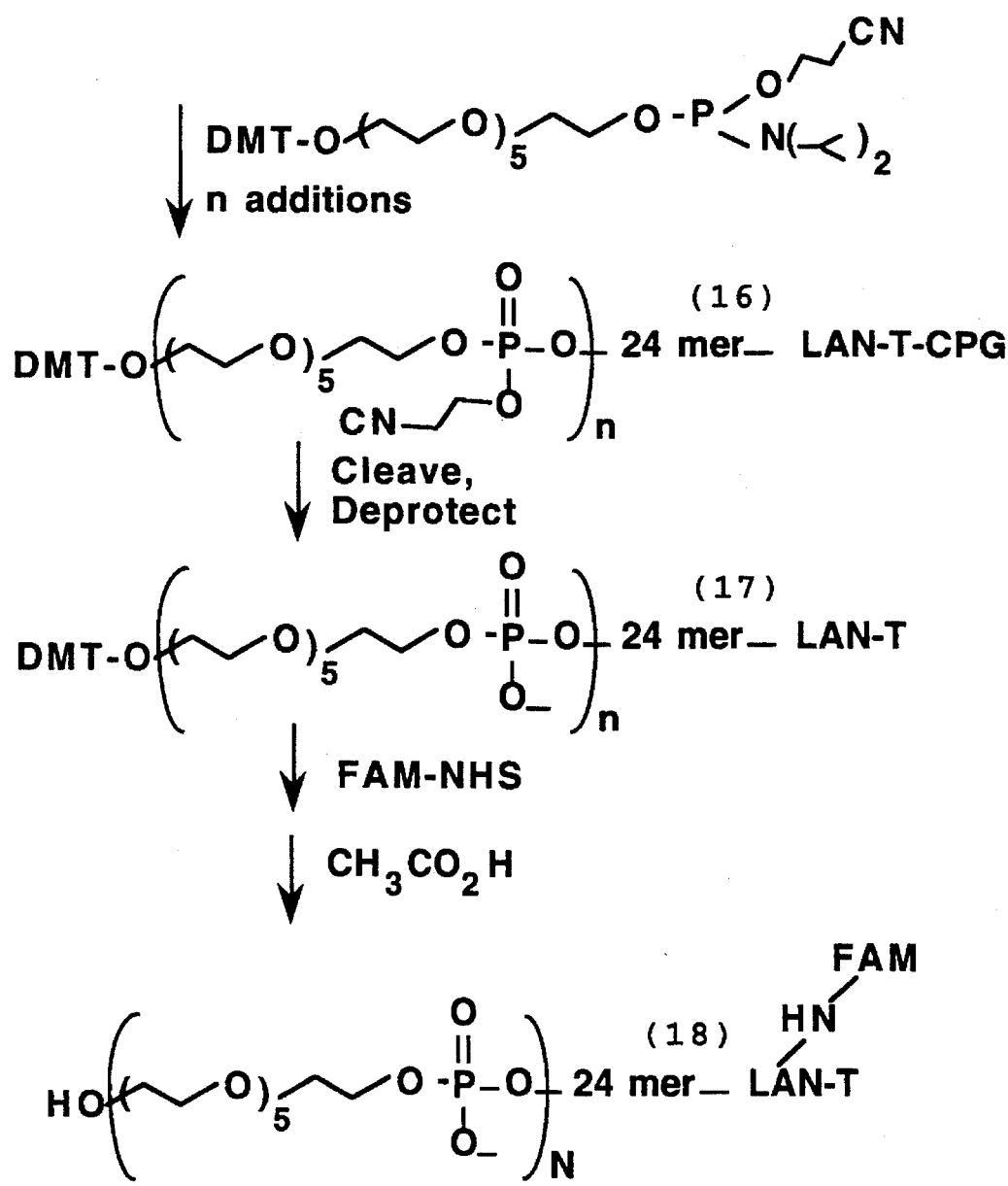
FIG. 5 shows reaction steps for adding HEO units successively to an oligonucleotide through phosphodiester linkages, and subsequent fluorescent tagging.
Figure 6:
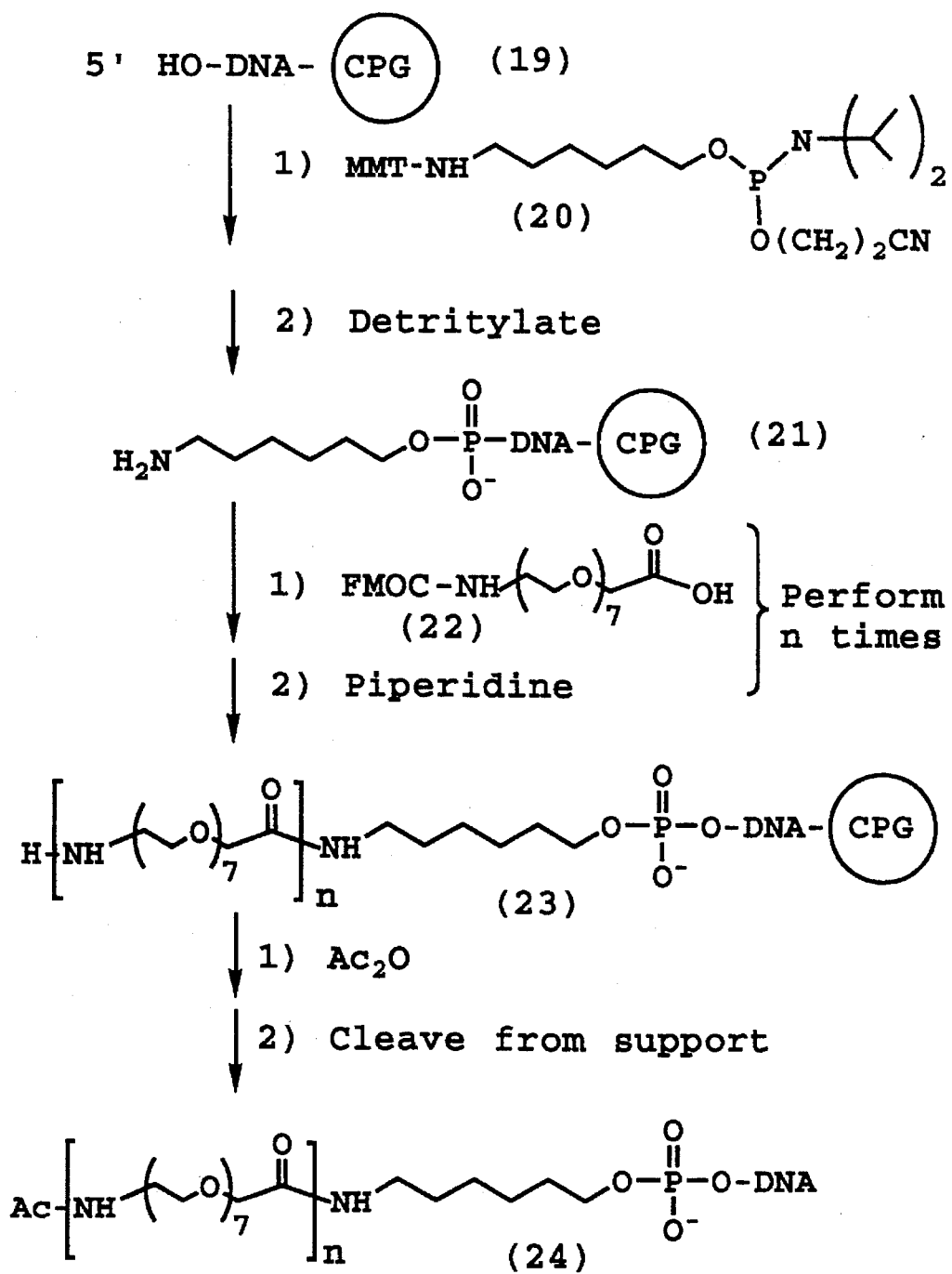
FIG. 6 shows reaction steps for adding polyethylene oxide polymer chains in which heptaethylene oxide units are linked by amide linkages.

FIG. 5 illustrates the stepwise addition of HEO units to an oligonucleotide formed by solid-phase synthesis on a solid support. The method follows generally the same phosphoramidite activation and deprotection steps used in building up the stepwise nucleotide addition. Details are given in Example 4.

Stepwise addition of heptaethylene oxide units to an immobilized oligonucleotide, via amide linkages, is illustrated in FIG. 6. The chemistry is similar to that used in regular peptide synthesis.

Also useful are polymer chains which contain polyethylene oxide units linked by phosphoramidate linking groups, wherein aminoalkyl branching groups are attached to the phosphoramidate groups (Agrawal, 1990).

As noted above, the polymer chain imparts to a probe, an electrophoretic or chromatographic mobility which is distinctive for each different-sequence probe. The contribution which the polymer chain makes to the mobility of the derivatized binding polymer will in general depend on the subunit length of the polymer chain. However, addition of charge groups to the polymer chain, such as charged linking groups in the PEO chain, or charged amino acids in a polypeptide chain, can also be used to achieve a selected mobility for a probe.

III. Separation and Detection of Labeled Probe Compositions

According to an important feature of the invention, different-sequence polynucleotides which themselves are difficult to resolve by chromatographic or electrophoretic methods, can be finely resolved via polymer chains attached to the binding polymers. The method is particularly useful in resolving polynucleotide-containing probes whose polynucleotide portions are substantially the same in length. One advantage of this feature is that the probe pairs used in the method can be designed to have substantially the same hybridization kinetics.

A. Separation of Probes by Chromatography

In one aspect of the invention, labeled, different-sequence probes are resolved (separated) by liquid chromatography. Exemplary solid phase media for use in the method include reversed-phase media (e.g., C-18 or C-8 solid phases), ion exchange media (particularly anion exchange media), and hydrophobic interaction media. In a related embodiment, the labeled, different sequence probes can be separated by micellar electrokinetic capillary chromatography (MECC).

Reversed-phase chromatography is carried out using an isocratic, or more typically, a linear, curved, or stepped solvent gradient, wherein the level of a nonpolar solvent such as acetonitrile or isopropanol in aqueous solvent is increased during a chromatographic run, causing analytes to elute sequentially according to affinity of each analyte for the solid phase. For separating polynucleotides, an ion pairing agent (e.g., a tetraalkylammonium species) is typically included in the solvent to mask the charge of phosphate oxyanions.

The mobility of a probe can be varied by addition of polymer chains that alter the affinity of the probe for the solid phase. Thus, with reversed phase chromatography, an increased affinity of the probe for the solid phase can be attained by addition of a moderately hydrophobic polymer (e.g., PEO-containing polymers, short polypeptides, and the like) to the probe. Longer attached polymers impart greater affinity for the solid phase, and thus require higher non-polar solvent concentration for the probe to be eluted (and a longer elution time).

Use of attached polymers for imparting separability to probes which contain identical polynucleotide portions is illustrated in Examples 6 and 7. As described in Example 6, a mixture of 25-mer oligonucleotide derivatives represented by formula 24 in FIG. 6, which contained polymer chains with 0 to 4 polymer units, was subjected to reversed phase HPLC (high performance liquid chromatography) on a C-18 column. The oligonucleotide derivatives were eluted using a linear gradient of acetonitrile in 0.1M triethylammonium acetate (10–25% acetonitrile over 30 min).

Figure 7:
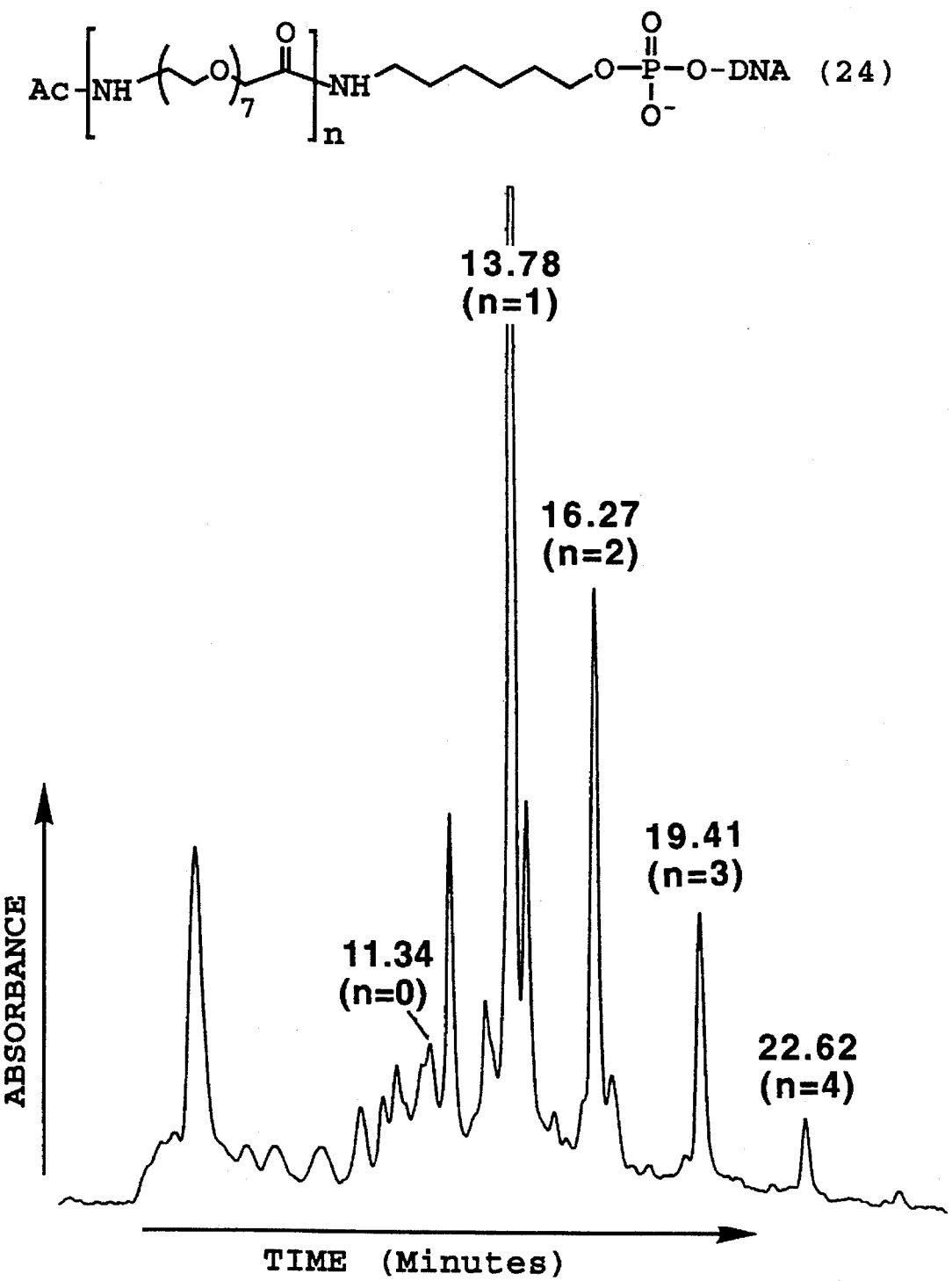
FIG. 7 shows separation by HPLC of selected derivatized polynucleotide species represented by formula 24 in FIG. 6 (n=1–4)

As can be seen from the chromatogram shown in FIG. 7, the acetylated 25-mer which contained zero HAA units (HAA=—NH(CH$_2$CH$_2$O)$_7$CH$_2$CO—) eluted first, with an elution time of 11.34 minutes. The 25-mer derivatives which contained 1, 2, 3 and 4 HAA units eluted later, with elution times of 13.78, 16.27, 19.41, and 22.62 minutes, respectively (the other peaks in the chromatogram correspond to impurities which were not removed prior to chromatography).

In anion exchange chromatography, analytes are eluted from a positively charged solid phase using a salt gradient, where analytes elute according to the number and distribution of negative charges in each analyte. As polyanions, polynucleotides elute according to the length of the polynucleotide, with the smallest polynucleotides eluting first, and longer polynucleotides eluting as the concentration of salt is increased over time. Thus, where anion exchange chromatography is used in the method of the invention, the polymer chains attached to the probes may be charged; positively charged polymer chains can be used to reduce the affinity of a probe for the solid phase, and negatively charged probes can be used to increase affinity for the solid phase.

Similar considerations apply to hydrophobic interaction chromatography.

In micellar electrokinetic capillary chromatography (MECC), polynucleotides may be separated by electrophoretic passage through a separation medium that contains micelles formed by surfactant molecules (e.g., sodium dodecyl sulfate). Sample separation is mediated by partitioning of the sample components between a primary phase, formed by the running buffer, and a secondary phase, formed by micelles, in a separation process that may be characterized as a form of chromatography. For enhanced polynucleotide separation, the separation medium may contain divalent metal ions, for complexing with sample polynucleotides to modify polynucleotide mobilities (Grossman et al., 1992; Cohen et al., 1987).

B. Separation of Probes by Electrophoresis in Sieving Matrix

According to another aspect of the invention, the labeled, different-sequence probes of the invention can be resolved by electrophoresis in a sieving matrix. Preferably, the electrophoretic separation is carried out in a capillary tube. Sieving matrices which can be used include covalently crosslinked matrices, such as acrylamide covalently crosslinked with bis-acrylamide (Cohen et al., 1990); gel matrices formed with linear polymers (Matthies et al., 1992); and gel-free sieving media (Zhu et al. 1992), for example. The percentage of acrylamide in polyacrylamide-containing matrices can range from about 3.5% for separating fragments in the 100–1000 base range, to about 20% for achieving separations in the 10–100 base range. The electrophoresis medium may contain a denaturant, such as 7M formamide, for maintaining polynucleotides in single stranded form.

In a sieving matrix, the mobility of non-derivatized polynucleotides depends on net charge and on size, with smaller polynucleotides migrating more rapidly than larger polynucleotides. Thus, any polymer chain (e.g., FIG. 3) can be used to impart lower probe mobility, by increasing the overall size of the probe to which the polymer chain is attached. In a preferred embodiment, the attached polymer chains are uncharged. A positively charged polymer chain (such as described by Agrawal et al., 1990) can be used for reducing probe mobility, since positive charge in the polymer chain will reduce the net charge of the probe, and thus, the net electrical force which is effective to draw the probe through the electrophoretic medium.

C. Probe Detection

For detection purposes, the probes of the invention contain, or can be modified to contain, a reporter label which allows direct detection of a labeled probe by a suitable detector, or a ligand, as set forth in Section I above.

Preferably, the reporter label is a fluorescent label which, more preferably, is spectrally resolvable as defined in Section I. For example, the reporter label may be attached to the 5' or 3'-terminal base of the polynucleotide portion of the probe, by methods known in the art (see Fung et al, U.S. Pat. No. 4,855,225; Prober et al, Science 238, 4767–4771 (1987); Smith et al., Nucleic Acids Res. 13, 2399–2412 (1985) or the like).

Exemplary dyes which can be used include 5- and 6-carboxyfluorescein, 5- and 6-carboxy-4,7-dichlorofluorescein, 2',7'-dimethoxy-5- and 6-carboxy-4,7-dichlorofluorescein, 2',7'-dimethoxy-4',5'-dichloro-5- and 6-carboxyfluorescein, 2',7'-dimethoxy-4',5'-dichloro-5- and 6-carboxy-4,7-dichlorofluorescein, 1',2',7',8'-dibenzo-5- and 6-carboxy-4,7-dichlorofluorescein, 1',2',7',8'-dibenzo-4',5'-dichloro-5- and 6-carboxy-4,7-dichlorofluorescein, 2',7'-dichloro-5- and 6-carboxy-4,7-dichlorofluorescein, and 2',4',5',7'-tetrachloro-5- and 6-carboxy-4,7-dichlorofluorescein. The above-mentioned dyes are disclosed in the following references which are incorporated by reference: Hobb, Jr. U.S. Pat. No. 4,997,928; Fung et al, U.S. Pat. No. 4,855,225; and Menchen et al, PCT application US90/06608. Alternatively, probes of the invention may be labelled with spectrally resolvable rhodamine dyes which are taught by Bergot et al, PCT application US90/05565.

IV. Assay Method

In one aspect, the method of the invention is designed for detecting one or more different-sequence regions in a target polynucleotide. In the method, a plurality of sequence-specific probes of the type described above are added to a target sequence. The probes are reacted with the target polynucleotide under conditions which favor sequence-specific binding of the probes to corresponding sequences in the target polynucleotide. As indicated above, this binding typically involves hybridization of complementary base sequences in the target and probe by Watson-Crick base pairing.

Alternatively, base-specific hydrogen-bond pairing between a single-strand probe and double-stranded target sequences, via Hoogstein base pairing, typically in the major groove of the duplex molecule (Kornberg), is also contemplated.

Following probe binding to the target polynucleotide, the probes are treated to selectively label probes bound to the target sequences in a sequence-specific manner, to produce modified labeled probes, each having a distinctive mobility in selected chromatographic or electrophoretic conditions. The modifying step may involve joining probe elements by ligation, such as enzymatic ligation, across an expected mutation site, primer-initiated amplification of selected target sequences, probe extension in the presence of labeled nucleoside triphosphate molecules, or enzymatic cleavage of a probe bound to a target region, as described in subsections A–E below.

The labeled probes produced by selective modification of target-bound probes are fractionated by electrophoretic or chromatographic methods, as discussed in Section III above. The migration rates of the modified, labeled probes can be used to identify the particular sequence associated with the labeled probes, to identify the presence of particular sequences in the target polynucleotide.

In a preferred embodiment, the probes can be probe pairs, each probe pair having two polynucleotide probe elements which are complementary in sequence to adjacent portions of a selected target sequence. A polymer chain for modifying electrophoretic or chromatographic mobility is attached to one of the probe elements, and a detectable reporter label is attached to the other probe element. The probes are hybridized to a target polynucleotide and then treated under conditions effective to ligate the end subunits of target-bound probe elements when their end subunits are base-paired with adjacent target bases. The ligated probe pairs are then released from the polynucleotide and separated chromatographically or electrophoretically, as discussed above. The method is designed so that a target sequence is not reported as present in the sample unless the corresponding ligated probe pair is formed. Probe pairs which fail to ligate can be distinguished from ligated pairs because (i) the probe elements which do not contain reporter label are not detectable, and (ii) the probe elements which contain polymer label have mobilities which are substantially different from the mobilities of ligated probes pairs. Moreover, use of spectrally resolvable reporter labels allows ligated probes which have the same mobility in a selected separation medium to be distinguished on the basis of different spectral characteristics (e.g., with fluorescent labels that have different emission wavelengths).

A. Probe-Ligation Method

This embodiment is designed especially for detecting specific sequences in one or more regions of a target polynucleotide. The target polynucleotide may be a single molecule of double-stranded or single-stranded polynucleotide, such as a length of genomic DNA, cDNA or viral genome including RNA, or a mixture of polynucleotide fragments, such as genomic DNA fragments or a mixture of viral and somatic polynucleotide fragments from an infected sample. Typically, in the present embodiment, the target polynucleotide is double-stranded DNA which is denatured, e.g., by heating, to form single-stranded target molecules capable of hybridizing with probe binding polymers.

Figure 8A:
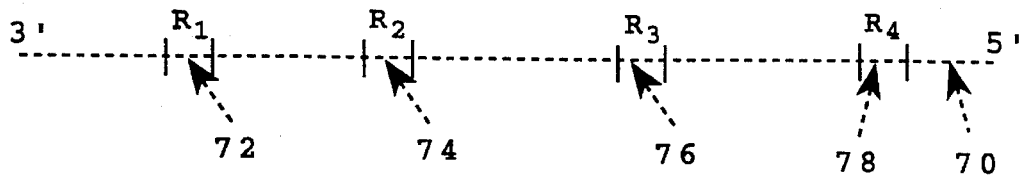
FIGS. 8A–8D illustrate an embodiment of the invention in which a target sequence is detected by ligation (OLA) of base-matched probe elements.

FIG. 8A shows a portion of a single-stranded target polynucleotide 70, e.g., the "+" strand of a double-stranded target, with the 3' to 5' orientation shown. The polynucleotide contains a plurality of regions $R_1$, $R_2$, $R_3$ to $R_n$, indicated at 72, 74, 76, and 78, respectively, which each contain a different base sequence. Each region preferably has about the same length, i.e., number of basepairs, preferably between about 20–80 basepairs. The total number of regions $R_n$ which are to be assayed in the method may be up to one hundred or more, although the method is also applicable where only a few different-sequence regions are to detected.

Although the method is illustrated in FIG. 8 with respect to a point mutation, it will be appreciated how other types of small mutational events, such as deletion or addition of one or more bases, can be detected by the method. More generally, the method can be used to assay, simultaneously, target sequences, such as sequences associated with a mixture of pathogen specimens, or gene sequences in a genomic DNA fragment mixture.

Figure 8B:
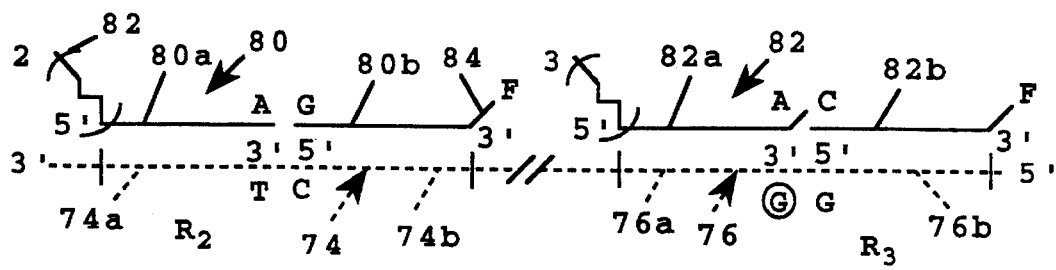
Figure 8C:
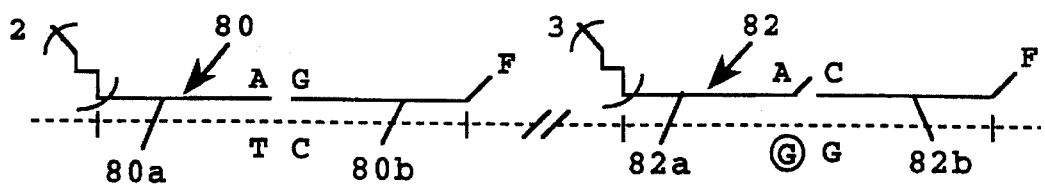

FIG. 8B shows an enlarged portion of target polynucleotide 70 which includes regions 74 ($R_2$) and 76 ($R_3$). Region 74 includes adjacent bases T and C, as shown which divide the region into two subregions 74a, 74b terminating at these two bases. The T and C bases are wildtype (non-mutated) bases, but one of these bases, e.g., the T base, corresponds to a known point-mutation site of interest. Similarly, region 76 includes adjacent bases G and G which divide this region into two subregions 76a, 76b terminating at these two bases. The G base in subregion 76a represents a point mutation from a wildtype T base, and the adjacent G base is non-mutated. The assay method is designed to identify regions of the target, such as regions 74 and/or 76, which contain such point mutations.

The probe composition used in the assay method is composed of a plurality of probe elements, such as those described with respect to FIG. 1B above. This composition is added to the target polynucleotide, with such in a denatured form, and the components are annealed to hybridize the probe elements to the complementary-sequence target regions, as shown in FIG. 1B.

One of the probes in the composition, indicated at 80, includes a pair of probe elements 80a, 80b whose sequence are complementary to the corresponding subregions 74a, 74b, respectively in region 74 of the target polynucleotide i.e., the probe element sequences correspond to those of the "–" strand of the $R_2$ region of the target. In particular, the probe elements have end-subunits A and G bases which, when the elements are hybridized to complementary subregions of region 74, as shown, are effective to form Watson-Crick base pairing with adjacent bases T and C in the target region.

Another of the probes in the composition, indicated at 82, includes a pair of probe elements 82a, 82b whose sequence are complementary to the corresponding subregions 76a, 76b, respectively in region 76 of the target polynucleotide. In this case, the probe elements have end-subunits A and C bases which, when the elements are hybridized to complementary subregions of region 76, as shown, are effective to form Watson-Crick base pairing with adjacent bases T and G bases in the wildtype target region. However, in the example shown, a T to G mutation prevents Watson-Crick base pairing of the A end-subunit to the associated target base.

Following annealing of the probe elements to corresponding target sequences, the reaction mixture is treated with ligating reagent, preferably a ligase enzyme, to ligate pairs of probe elements whose confronting bases are base-paired with adjacent target bases. Typical ligation reaction conditions are given in Example 8. The ligation reaction is selective for those probe elements whose end subunits are base-paired with the target bases. Thus, in the example illustrated (FIG. 8C), the probe elements 80a, 80b are ligated, but probe elements 82a, 82b are not.

It can be appreciated that the ligation reaction joins an oligonucleotide carrying a sequence-specific polymer chain to an oligonucleotide carrying a detectable reporter, selectively forming labeled, ligated probes, such as ligated probe 84, composed of an oligonucleotide labeled at one end with a probe-specific polymer chain and at its other end with a detectable (fluorescent) reporter.

Figure 8D:
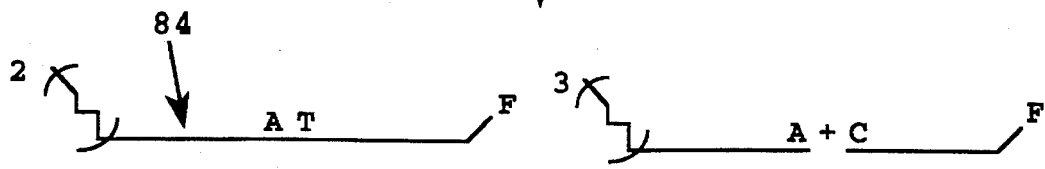

Denaturing the target-probe complexes, as illustrated in FIG. 8D, releases a mixture of ligated, labeled probes, corresponding to wildtype target sequences, and non-ligated probe elements corresponding to point mutations at or near probe element end subunits. Each ligated, labeled probe has a polymer chain which imparts to that probe, a distinctive mobility under selected chromatographic or electrophoretic conditions, as discussed above.

Figure 9:
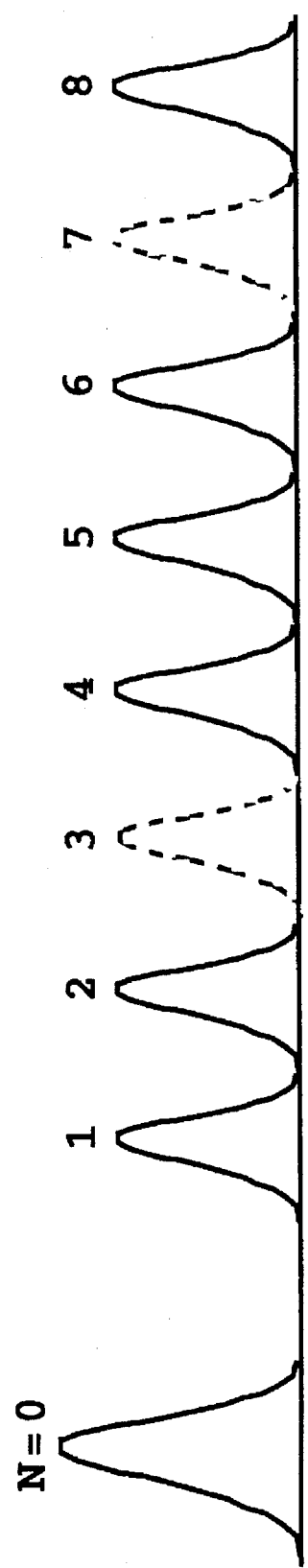
FIG. 9 illustrates an idealized electrophoretic pattern observed in the FIG. 8 method, where a target polynucleotide contains mutations in two different target regions.

In the assay method illustrated in FIGS. 8A–8D, one of the target regions ($R_3$) contains a mutation which prevents ligation of the complementary-sequence probe elements. It is assumed, by way of example, that the entire target polynucleotide contains eight sequence regions of interest, of which regions $R_3$ and $R_7$ have mutations of the type which prevent probe-element ligation, and the other six regions are wildtype sequences which lead to ligated, labeled probes. FIG. 9 shows an idealized chromatographic (or electrophoretic) pattern which would be expected in the ligation assay method. Peaks 1–8 in the figure are the expected elution times of ligated oligonucleotide probes having increasingly longer polymer chains, such as 1, 2, 3, 4, 5, 6, 7, and 8 linked HEO units. The observed chromatographic or electrophoretic pattern will show gaps at the 3 and 7 peak positions, as indicated, evidencing mutations in the 3 and 7 target positions. All unmodified DNA will elute substantially with the N=0 peak.

In the above OLA ligation method, the concentration of probe can be enhanced, if necessary, by amplification of the derivatized probes with repeated probe element hybridization and ligation steps. Simple additive (linear) amplification can be achieved using the target polynucleotide as a target and repeating the denaturation, annealing, and probe-element ligation steps until a desired concentration of derivatized probe is reached.

Figure 10A:
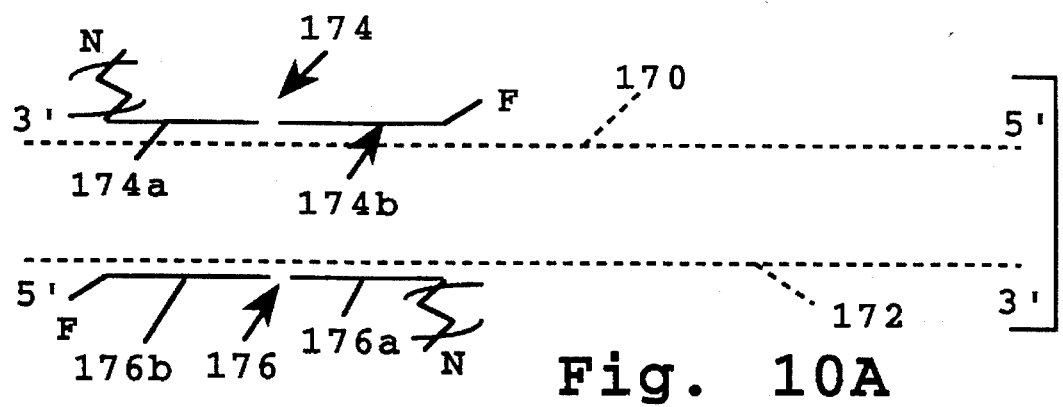
FIGS. 10A–10C illustrate an embodiment of the invention in which a mutation is detected by ligation of base-matched probes by ligase chain reaction (LCR) in accordance with the present invention.

Alternatively, the ligated probes formed by target hybridization and ligation can be amplified geometrically by ligase chain reaction (LCR), according to published methods (Winn-Deen), and also as described in Example 9. In this method, illustrated in FIGS. 10A–10C, two sets of sequence-specific probes, such as described with respect to FIG. 1B, are employed for each target region of a double-stranded DNA, whose two strands are indicated at 170 and 172 in FIG. 10A. One probe set, indicated at 174, includes probe elements 174a, 174b which are designed for sequence specific binding at adjacent, contiguous regions of a target sequence on strand 170, as indicated, and a second probe set, indicated at 176, includes probe elements 176a, 176b which are designed sequence specific binding at adjacent, contiguous regions of a target sequence on opposite strand 172, also as shown.

Figure 10B:
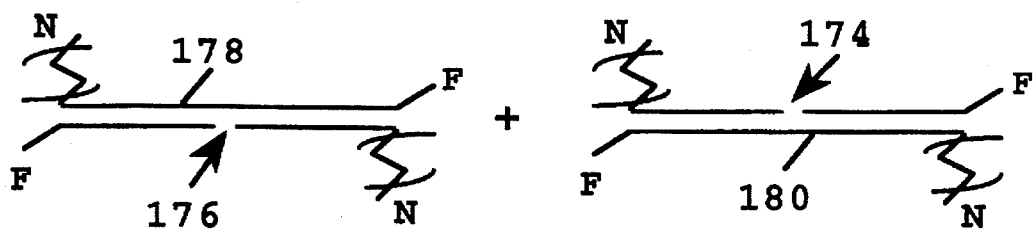
Figure 10C:
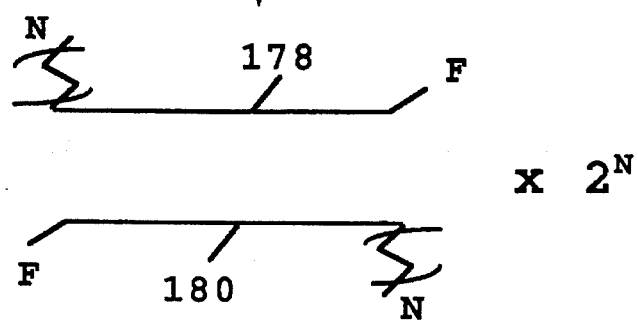

As seen, probe elements 174a and 176a are derivatized with a polymer chain, and probe elements 174b, 176b, with a fluorescent reporter, analogous to probe set 32 described above with respect to FIG. 1B. After hybridization of the two probe sets to the denatured single-stranded target sequences, the probe elements bound to each target region are ligated, and the reaction products are denatured to release labeled probes 178, 180 (FIG. 10B). These labeled probes can now serve as target substrates for binding of probe sets 174, 176, as shown in FIG. 10B, with ligation now producing $2^2$ labeled probes. This process is repeated, i.e., N-2 times, to produce ideally a total of $2^N$ labeled probes 178, 180, as indicated in FIG. 10C.

Although the probe-ligation method has been described above with respect to detecting mutations in each of a plurality of target regions, it is understood that the method is also applicable to detecting multiple target sequences related, for example, to the presence or absence of different pathogen sequences, or different genomic sequences in a higher organism.

Figure 17A:
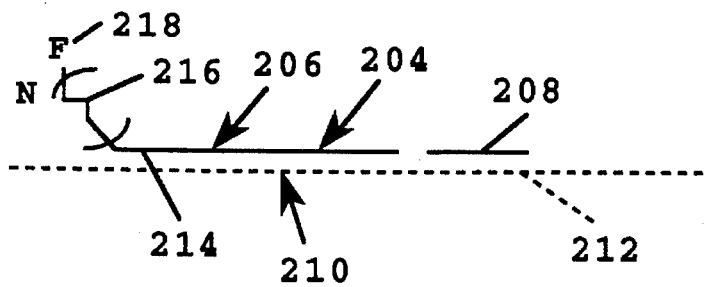
FIGS. 17A–17B illustrate an embodiment of a probe ligation method in accordance with the invention.
Figure 17B:
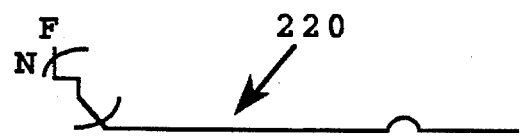

A modification of this general method is illustrated in FIGS. 17A and 17B. In this method, each sequence-specific probe, such as probe 204, includes a pair of probe elements, such as elements 206, 208, which are designed for binding to adjacent portions of selected sequence, such as sequence 210 in a target polynucleotide 212. Probe 206 includes a binding polymer 214, a polymer chain 216 which imparts a distinctive mobility to the probe element, and a reporter 218 which may be attached to the polymer chain or binding polymer. The second probe element is an oligonucleotide which is ligatable with probe element 206, when the two elements are hybridized to the associated target sequence, as described above with respect to FIGS. 8A–8D.

The probes are hybridized to the target polynucleotide, ligated, and released, as described above, to yield a modified (ligated) labeled probe 220. The mobility of ligated probe 220 is distinctive with respect to the mobilities of other ligated probes in the probe mixture by virtue of the attached polymer chain. The modified probes are then fractionated by chromatography or electrophoresis, as described above, to identify probes associated with different target sequences of interest.

Figure 15A:
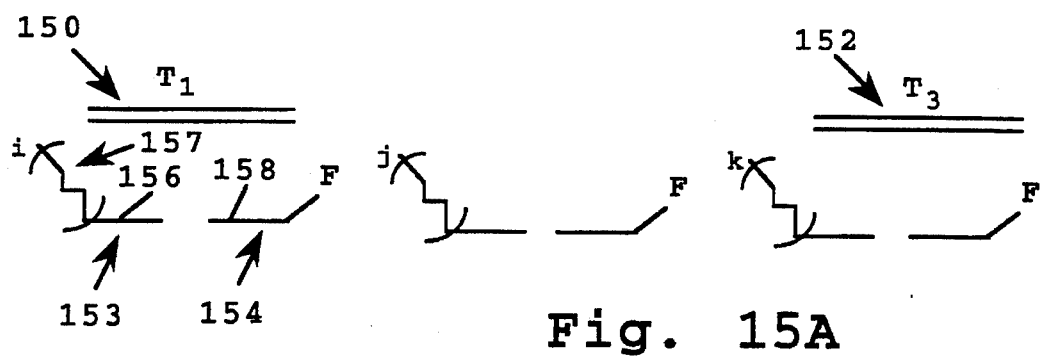
FIGS. 15A–15C illustrate a method for forming modified, labeled probes, in accordance with the method of the invention.
Figure 15B:
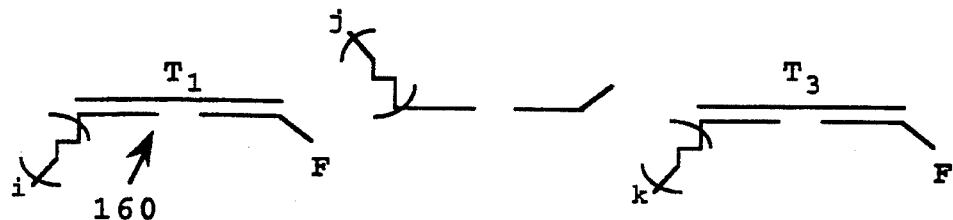
Figure 15C:
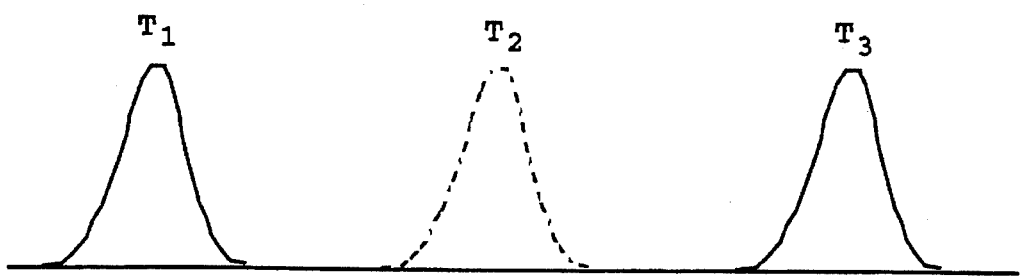

FIGS. 15A–15C illustrate a related method for modifying polynucleotide probes, in accordance with the invention. The method is used to detect the presence of one or more sequences $S_1$ to $S_n$ associated with fragments $T_1$ to $T_n$, such as double-stranded fragments $T_1$ and $T_3$ shown at 150, 152, respectively. The fragments are modified in this method by hybridizing with a probe composition which includes, for each target sequence of interest, a pair of probe elements, such as probe elements 152, 154 which have the general construction of the probe elements described in FIG. 1B. That is, the element 152 includes an oligonucleotide 156 designed for base specific binding to one region of fragment $T_1$, and a selected length polymer chain 157, and element 154 is a reporter-labeled oligonucleotide 158 designed for base-specific binding to a second region of the fragment. As shown in FIGS. 15A and 15B, probes for target sequence $T_1$, $T_2$, and $T_3$ include polymer chains (i, j, and k, respectively) which impart a distinctive mobility to the binding polymers to which the polymer chains are attached.

In the method, the fragments are modified by hybridization, in single-stranded form, with the probe elements in the probe composition forming hybridized fragments, such as fragment 160, with one probe having a selected-length polymer chain and a second reporter-labeled probe. The target fragment may be thought of in this method as serving a probe-ligating function to join the two probe elements. Since the fragment itself does not appreciably change the mobility of the joined probe elements, the method allows for identification of target sequence fragments according to the distinctive mobility imparted by the polymer chain in one of the probe elements. In FIG. 15C, two peaks are observed, corresponding to fragments $T_1$ and $T_3$ in the mixture. The absence of a peak corresponding to fragment $T_2$ (dashed lines in FIG. 15C) indicates that $T_2$ is not present in the sample.

B. Target-Sequence Amplification

In a second general embodiment of the method, illustrated in FIG. 11, the probes are designed for primer-initiated amplification of one or more regions of the double-stranded target polynucleotide. At least one strand of the amplified target regions carries a polymer chain which imparts to each amplified fragment, a distinctive mobility. The amplified regions may be reporter-labeled during or after amplification.

Figure 11A:
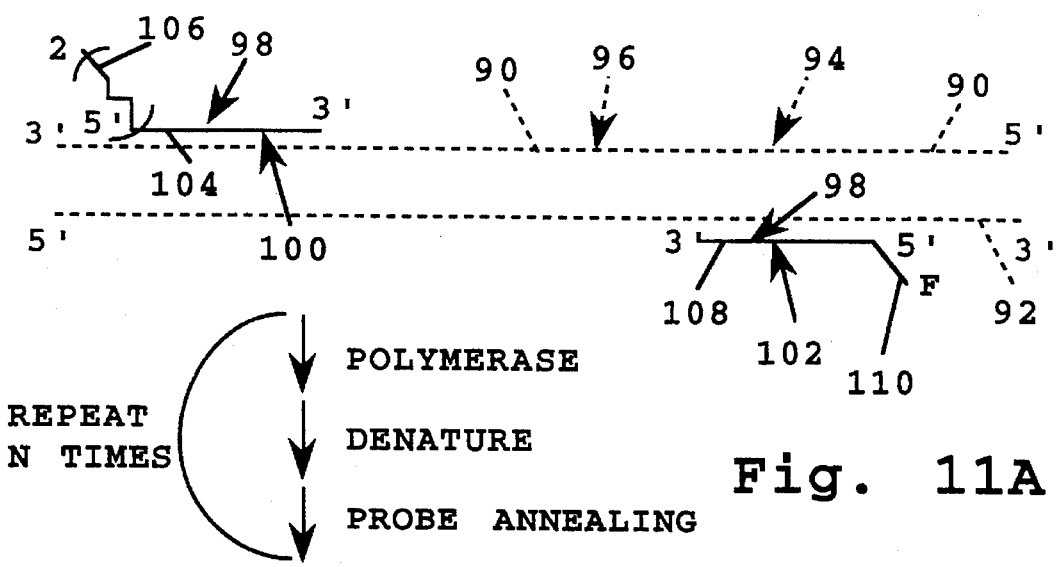
FIGS. 11A–11B illustrate the steps in an embodiment of the invention, using primer-initiated amplification to produce double-stranded labeled probes.
Figure 11B:
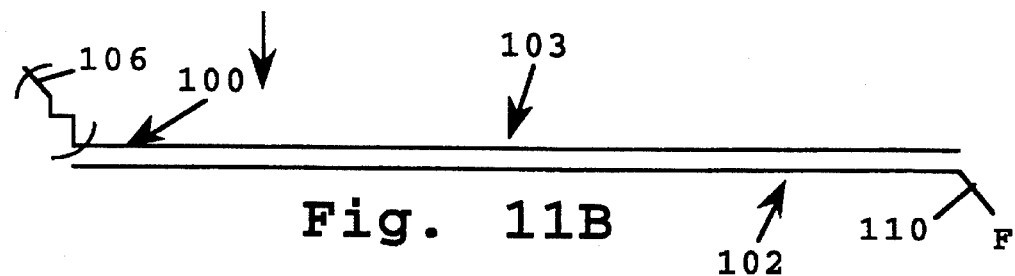

FIGS. 11A and 11B illustrate the method. The figure shows the two separate strands 90, 92 of a normally double-stranded target polynucleotide 94 having at least one, and typically a plurality of regions, such as region 96, to be amplified. The target is reacted with a probe composition whose probes each consist of a pair of primer elements, such as primer elements 52, 54, in probe 50 described above with respect to FIG. 1C. FIG. 11A shows a probe 98 composed of primer elements 100, 102. Primer element 100 consists of an oligonucleotide primer 104 designed for hybridization to a 3' end of one strand of region 96, which carries at its 5'-end, a selected-length polymer chain 106, similar to above-described primer element 52. Element 102 is an oligonucleotide primer designed for hybridization to a 5' end of the opposite strand region 96, which carries a fluorescent reporter at its 5'-end.

In practicing this embodiment of the method, the probe composition is reacted with the target polynucleotide under hybridization conditions which favor annealing of the primer elements in the probe composition to complementary regions of opposite target polynucleotide strands, as illustrated in FIG. 11A. The reaction mixture is then thermal cycled through several, and typically about 20–40, rounds of primer extension, denaturation, primer/target sequence annealing, according to well-known polymerase chain reaction (PCR) methods (Mullis, Saiki). One amplified region, generated by the probe primers 100, 102, is shown at 100 in FIG. 11B.

If, as in the example illustrated, one of the primers is reporter-labeled, the double-stranded amplified region, such as region 103, forms a labeled probe having a polymer chain carried on one strand and a reporter on the other strand. Alternatively, the amplified sequences may be labeled in double-stranded form by addition of an intercalating or cross-linking dye, such as ethidium bromide. The different-sequence amplified probes can be fractionated in double-stranded form by chromatography or electrophoresis as described above, based on the different mobilities of the double-stranded species.

The just-described method is useful, for example, in assaying for the presence of selected sequences in a target polynucleotide. As an example, the target polynucleotide may be genomic DNA with a number of possible linked gene sequences. The probes in the composition are primer pairs effective in PCR amplification of the linked sequences of interest. After sequence amplification, the presence or absence of the sequences of interest can be determined from the positions or elution times of the labeled probes during an electrophoretic or chromatographic run.

In another application, it may be desired to assay which of a number of possible primer sequences, e.g., degenerate sequences, is complementary to a gene sequence of interest. In this application, the probe composition is used to amplify a particular sequence. Since each primer sequence will have a distinctive polymer chain, the primer sequence complementary to the sequence end regions can be determined from the migration characteristics of labeled probes. As with the other applications discussed above, the method may involve including in the fractionated probe mixture, a series of oligonucleotides derivatized with polymer chains of known sizes, and labeled different reporter groups that are carried on the test probes, to provide mobility standards for the chromatographic or electrophoretic separation.

Figure 12A:
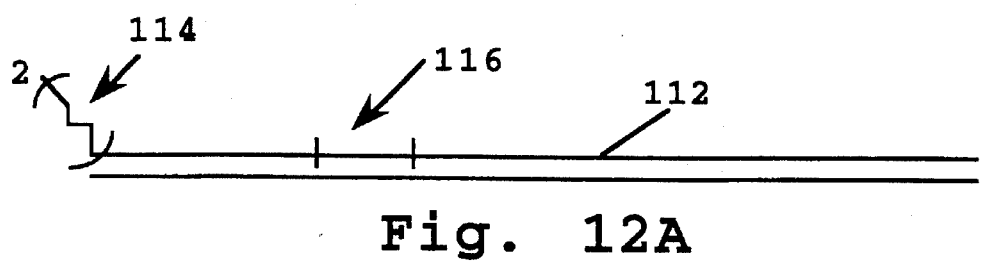
FIGS. 12A and 12B illustrate an alternative method for labeling amplified target sequences formed in the FIG. 12 method.
Figure 12B:
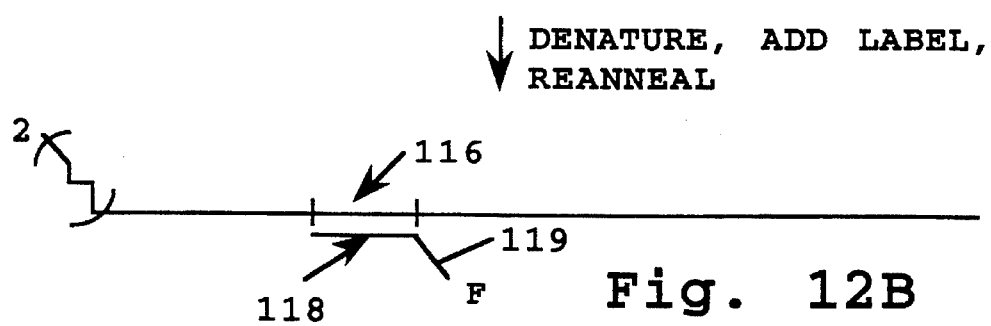

In still another application, the amplified target fragments are labeled by hybridizing to the amplified sequences, with such in single-stranded form, a reporter-labeled probe. This application is illustrated in FIGS. 12A and 12B, which show an amplified target sequence 112 having a polymer chain 114 carried on one strand. The aim of the assay is to determine whether any, and if so which, of the one or more fragments produced by the primer probes contains a sequence complementary to the probe sequence. In this example, the fragment 112 contains a region 116 whose base sequence is complementary to that of a known-sequence probe 118.

The fragments, such as fragment 112, are hybridized with the one or more labeled probes under standard hybridization conditions, binding probe 118 to the strand of fragment 116 which contains the polymer chain, thus forming labeled probes which can be fractionated by chromatography or electrophoresis methods, as above.

Figure 14A:
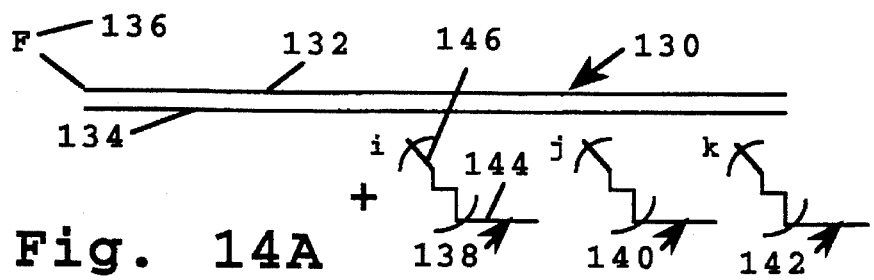
FIGS. 14A and 14B illustrate another method of modifying known-sequence polynucleotide fragments, in accordance with the method of the invention.
Figure 14B:
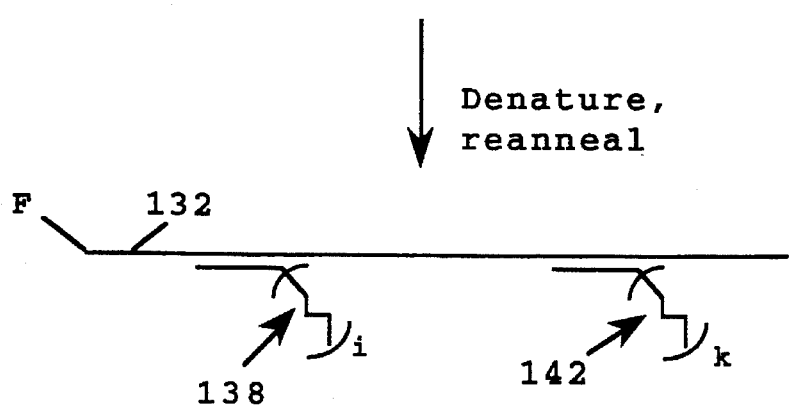

FIGS. 14A and 14B illustrate another method for modifying PCR-generated target fragments, such as double-stranded fragment 130, composed of strands 132, 136. In the embodiment illustrated, strand 132 has been fluorescent-labeled with a reporter 134 at one fragment end during amplification. The fragment strand can be reporter labeled by a variety of methods, such as by nick translation or homopolymer tailing in the presence of labeled dNTP's, or by PCR amplification using a reporter-labeled primer.

The amplified fragments are mixed with a probe composition that includes a plurality of probes, such as probes 138, 140, 142, designed for sequence-specific binding to different-sequence regions of one strand of the target. Probe 138, which is representative, includes an oligonucleotide 144 having the desired region-specific base sequence, and a polymer chain 146 which imparts to each different-sequence probe, a distinctive mobility.

In the method, the fragments are modified by hybridization, in single-stranded form, with the probes in the probe composition, forming fragments, such as fragment 150, with one or more double-stranded regions corresponding to probe binding. The modified fragments are reporter labeled in one strand and derivatized with one or more selected-length polymer chains in opposite strand probes. The modified fragments are then fractionated in double-stranded form to fractionate the fragments according to the number and size of polymer chains associated with each fragment.

Thus, for example, in the method illustrated, the fragment 132 binds probes 138, 142, and thus has been modified to carry a total of i+k polymer chain units. Since the fragments will migrate with migration times which are dependent on the total number of polymer chain units attached to the fragments, the probe(s) associated with each fragment can be identified. This method can be used, for example to examine the distance between known sequences within genomic DNA, or for identifying linked sequences.

C. Probe Extension

Figure 13A:
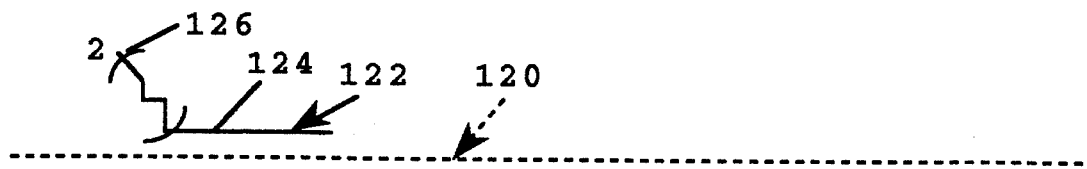
FIGS. 13A and 13B illustrate steps in an embodiment of the invention, using reporter-labeled nucleotide addition to the target-bound probes to form labeled probe species.
Figure 13B:
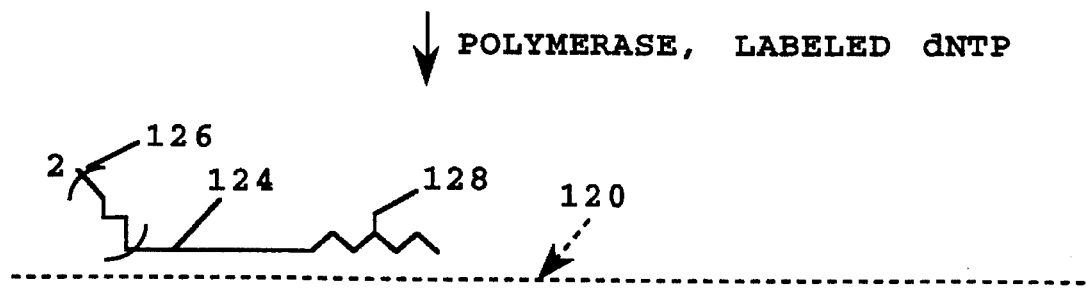

A third general method for forming labeled probes, in accordance with the method of the invention, is illustrated in FIGS. 13A and 13B. In this method, a single-stranded target polynucleotide, such as shown at 120 in the figures, is reacted with a probe composition containing a plurality of probes, such as probe 122 which are designed for base specific binding to selected regions of the target. Probe 122, which is representative, is like probe 20 in FIG. 1A, and includes an oligonucleotide having a free 3'-end OH group and a selected-length polymer chain carried at its 5' end.

After binding the probes to the target, the probes are treated with DNA polymerase I, in the presence of at least one reporter-labeled dNTP, as shown. Dye-labeled dNTPs can be synthesized from commercial starting materials. For example, amino 7-dUTP (Clontech, Palo Alto, Calif.) can be reacted with fluorescein NHS ester (Molecular Probes, Eugene, Oreg.) under standard coupling conditions to form a fluorescein-labeled dUTP. The polymerase is effective, in the presence of all four nucleoside triphosphates, to extend the 3' end of target-bound probes, incorporating one or more labeled nucleotides, as indicated at 128, to form the desired labeled probes having polymer chains which are characteristic of each probe sequence. Alternatively, in the above example, fluorescein may be coupled to the modified nucleotide, e.g., amino-7-dU, after incorporation into the probe.

After probe extension, the probes are released from the target and fractionated by chromatography or electrophoresis, as above, to identify the mobilities of the labeled probes corresponding to sequences contained in the target nucleotide.

D. Fragment Cleavage

Figure 16A:
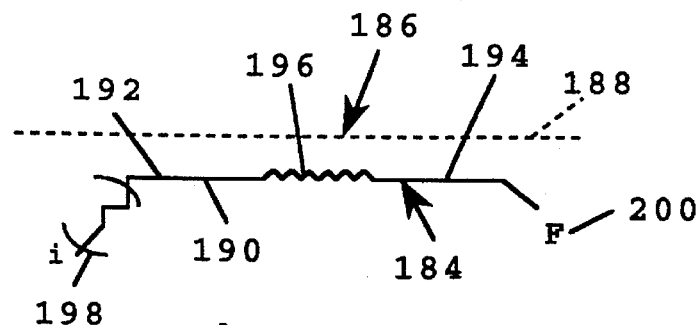
FIGS. 16A and 16B illustrate an alternative method for forming modified, labeled probes, in accordance with another embodiment of the invention.
Figure 16B:
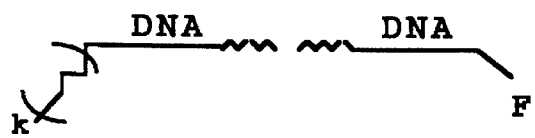

FIGS. 16A and 16B illustrate another embodiment of the method of the invention. In this method, the probe composition includes a plurality of sequence-specific probes, such as probe 184, designed for sequence specific binding to regions of a single-stranded target polynucleotide, such as region 186 in target polynucleotide 188. Probe 184, which is representative, includes a probe a binding polymer 190 composed of a first single-stranded DNA segment 192, and a second segment 194 which includes single-stranded RNA region 196. A polymer chain 198 attached to the binding polymer's first segment imparts to the binding polymer, a distinctive mobility, as discussed above. A reporter 200 (F) is attached to the second segment of the binding polymer. In particular, the polymer chain and reporter are on opposite sides of the RNA region, so that selective cleavage in this region will separate the probes first segment and attached polymer chain from the reporter.

In the method, the probe composition is reacted with the target polynucleotide under hybridization conditions, as above, to bind the probes in a sequence specific manner to complementary target regions. As seen in FIG. 16A, this produces a region of RNA/DNA duplex in each bound probe. The reaction mixture is now treated with a nuclease, such as RNase H, which is able to cut duplex RNA/DNA selectively (Duck), thus cutting each probe in its RNA binding region.

The hybridization reaction is now denatured, releasing, for each specifically bound probe, a modified labeled probe which lacks its polymer chain and thus now migrates as a free oligonucleotide by chromatography or electrophoresis. In an alternative embodiment (not shown), the polymer chain may be attached to reporter side of the probe, so that RNAse treatment releases a portion of the binding polymer, modifying the mobility of the remaining probe (which contains the polymer chain and reporter), thus shifting the mobility of the probe with respect to the uncleaved probe.

Figure 18A:
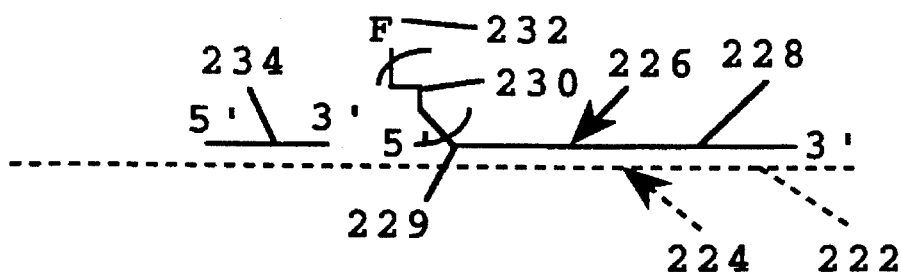
FIGS. 18A and 18B illustrate another method for forming modified, labeled probes, in accordance with the invention.

In another embodiment using the cleavage mode of generating labeled probe, probe modification is accomplished during extension of a primer annealed to the target polynucleotide upstream from (beyond the 5' end of) the annealed probe. This extension is produced by a DNA polymerase also incorporating a 5' to 3' exonuclease activity (Holland). The method is illustrated in FIG. 18 which shows a target polynucleotide 222 with a sequence region 224 of interest. The probes in this method are exemplified by probe 226 which contains a binding polymer 228 having a subunit 229 adjacent the polymer's 5' end. Attached to this base are a polymer chain 230 and a labeled probe 232 (which may be attached to the free end of the polymer chain). Also shown in the figure is a primer 234 which is designed for sequence specific binding to the target, upstream of the region 224.

Figure 18B:
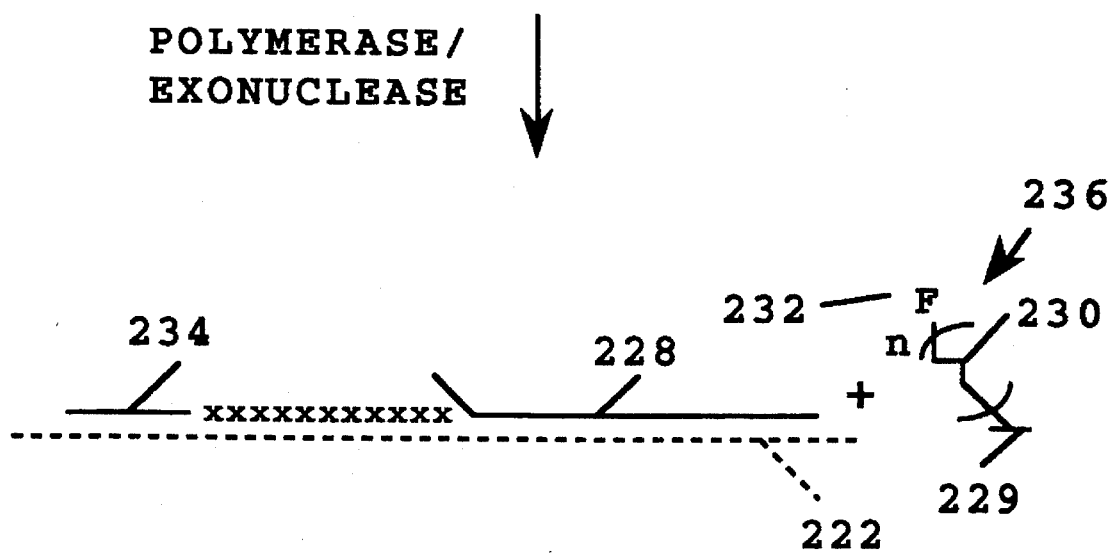

In practicing the method, the sequence-specific probes and a set of primers, such as primer 234, are reacted with the target polynucleotide under hybridization conditions, to bind associated probes and upstream primers to different-sequence regions of the target. The target and attached probes are now treated with the above polymerase in the presence of all four nucleoside triphosphates, resulting in polymerization of the primer in a 5' to 3' direction, as indicated by x's in FIG. 18B. As the polymerase reaches the 5' end of the adjacent probe, it displaces the probe from the target region, and also cleaves off 5' end subunits from the probe. As shown in FIG. 18B, cleavage of the subunit 229 from the probe releases a labeled probe 236 composed of base 229, reporter 232, and polymer chain 230 which imparts to the probe, a distinct mobility.

It will be recognized by one skilled in the art of molecular biology that many variants of the cleavage mode are practical; using exonuclease activities not linked to polymerase activities (e.g., the N-terminal selective cleavage fragment from *E. coli* polymerase I and the exonuclease of bacteriophage λ), using the 3'→5' proofreading exonuclease activities of certain DNA polymerases (in which case the polymer chain 198 and the reporter F preferably are attached to the 3' end of the probe, and this 3' end comprises one or more nucleotides mismatched to the template polynucleotide 188 of FIG. 16A), or using any of a wide range of sequence-specific endonucleases such as the restriction endonucleases. In all of these cases, the preferred embodiment locates the reporter and the polymer chain on the same side of the cleavage site(s), such that they remain covalently linked subsequent to cleavage. Additional polymer chains may or may not be added to the probe on the opposite side of the cleavage site(s) from the reporter in order to optimize the resolution of labeled probes from unlabeled probes.

E. Probe Capture

Figure 19A:
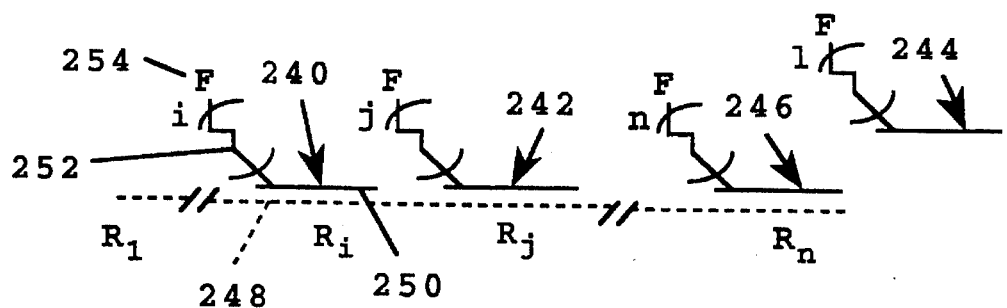
FIGS. 19A–19C illustrate another embodiment of the invention, wherein probes are hybridized to a target polynucleotide immobilized on a solid support.
Figure 19B:
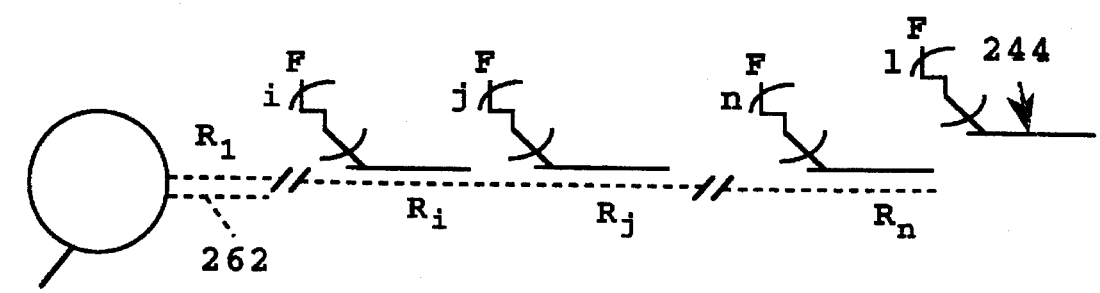
Figure 19C:
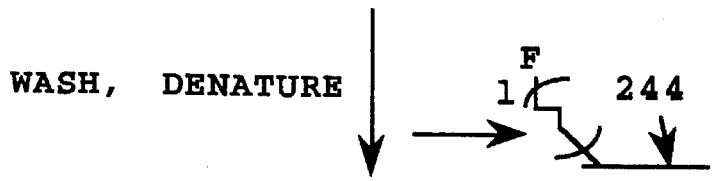
Figure 19C:
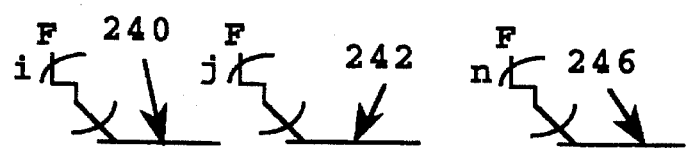

Another general embodiment, illustrated in FIGS. 19A–19C, involves probe capture and release from an immobilized target polynucleotide. FIG. 19A shows the addition of a plurality of probes, such as probes 240–246 to a target polynucleotide 248 containing different-sequence regions of interest, such as $R_i$, $R_j$, and $R_n$. Probe 240, which is representative, includes a binding polymer 250, a polymer chain 252 which imparts to that probe, a distinctive mobility, and a reporter 254 attached to the polymer chain. In the embodiment shown, each different-sequence probe has a different length polymer chain for achieving the distinctive mobility.

The probes are reacted with the target polynucleotide under hybridization conditions, as above. In the method illustrated in FIG. 19A, probes 240, 242, and 246 each hybridize with a complementary sequence in regions $R_i$, $R_j$, and $R_n$, respectively, of the target polynucleotide. It is assumed in this example that the target polynucleotide does not contain a region complementary to probe 244, leaving this probe unbound.

The target and hybridized probes are then treated to immobilize the target polynucleotide. This is done in the present example by adding a solid support 260 derivatized with an oligonucleotide probe 262 which is complementary to a region $R_1$ of the target polynucleotide, thus binding the target to the solid support, as indicated in FIG. 19B. The support and attached target and probes are now washed to remove non-specifically bound probes, such as probe 244. In the final treating step, the washed solid support mixture is denatured to release bound probes, such as probes 240, 242, and 246, and these probes are then fractionated by electrophoresis or chromatography, as above, to identify target sequences, on the basis of distinctive electrophoretic positions and/or reporter combinations of the fractionated, labeled probes.

From the foregoing, it will be appreciated how various objects and features of the invention are met. The method allows a plurality of target sequences to be assayed in a single-assay format, with rapid identification of sequences according to the mobilities of different polymer chains associated with sequence-specific labeled probes.

The polymer chains allow for separation of single and double stranded oligonucleotides, in a simple chromatography or electrophoresis method. In particular, the method allows for effective fractionation of a plurality of oligonucleotides, all of which have similar or identical sizes. One advantage of this feature is that the polynucleotide portions in the probes used in the method can all have similar or the same sizes, and thus can be hybridized with target sequences with about the same hybridization kinetics and thermodynamics ($T_m$).

The probes of the invention can be readily synthesized by conventional solid-phase methods. In one method, a polymer chain of a selected number of units can be formed directly on an oligonucleotide, by conventional solid-phase synthesis methods.

The following examples describe various aspects of making and using polymer-chain probes. The examples are intended to illustrate, but not limit the scope of the invention.

Materials

Hexaethylene glycol, 4,4'-dimethoxytrityl chloride, triethylamine, diisopropylethylamine, acetic acid, pyridine, methanesulfonyl chloride, sodium hydride, 2-cyanoethyl-N,N,N',N' -tetraisopropylphosphorodiamidite were obtained from Aldrich, Milwaukee, Wis. Diisopropylamine tetrazole salt, FAM-NHS/DMSO JOE-NHS/DMSO and TAMRA-NHS/DMSO were obtained from Applied Biosystems (ABI), Foster City, Calif. LAN (Linker Arm Nucleotide)

5'-dimethoxytrityl- 5-(N-(7-trifluoroacetylaminoheptyl)-3-acrylamide)-2'-deoxyuridine-3'-phosphoramidite was obtained from Molecular Biosystems, Inc., San Diego, Calif.

Sephadex G-25M PD-10 columns were obtained from Pharmacia, Uppsala, Sweden. Derivatized oligonucleotides were LC purified using an ABI RP-300 (C8) column (4.6× 220 mm) using a flow rate of 1.5 ml/min and a gradient of 0.1M triethylammoniumacetate/water pH 7.0 and acetonitrile.

DNA synthesizer: 380B, ABI, Foster City, Calif.

Example 1

Synthesis of (HEO)$_N$ Chains

The reactions described in this example are illustrated in FIG. 2 and are similar to those of Cload and Schepartz.

A. Dimethoxytrityl (DMT)-protected hexaethylene oxide (HEO)

27.0 gm (95.6 mmol) of HEO was dissolved in 100 ml pyridine. To this solution at room temperature was added a solution of 27.0 gm (79.7 mmol) of dimethoxytrityl chloride in 150 ml pyridine over 10 hr. The reaction was stirred at room temperature overnight (15 hr.) The solvent was removed in vacuo and the residue was brought up in 150 ml EtOAc and 100 ml H$_2$O, 2×100 ml brine and the organic layer was dried over Na$_2$SO$_4$. The solvent was removed to give a dark orange oil (38.36 gm). The crude material was purified by silica gel chromatography using 200 gm kiesel gel 60 and eluting with 2% methanol-methylene chloride (silica gel was basified with triethylamine). Appropriate fractions were combined to give 29.52 gm (50.49 mmol) of compound 1. Analysis of the DMT-protected HEO (compound 1 in FIG. 2) showed:

$^1$HNMR (300 MHz CDCl$_3$) δ7.5–6.8 (mult., 13H aromatic), 3.75 (S, 6H, OCH$_3$), 3.6 (20H, mult., OCH$_2$—CH$_2$O), 3.5 (2H, mult., CH$_2$—OH), 3.2 (2H, t, CH$_2$ODMT).

B. DMT-Protect HEO Phosphoramidite 1 gm (1.7 mmol) of DMT-protected HEO from Example 1A above and 0.029 g (0.17 mmol) of tetrazole diisopropyl ammonium salt were dissolved in 10 ml methylene chloride under inert atmosphere. To this was added 0.59 gm of 2-cyanoethyl tetraisopropyl phosphordiamidite, and the mixture was stirred overnight at room temperature. The reaction mixture was washed with a saturated solution of NaHCO$_3$, brine and dried over Na$_2$SO$_4$. The solvent was removed to give 1.58 gm crude oil, and the product was purified by flash chromatography through silica gel and eluted with 50% EtOAc-hexane (silica gel was basified with triethylamine). 0.8 gm (1.3 mmol) of purified phosphoramidite (compound 2 in FIG. 2) was recovered.

C. DMT-Protected HEO Methanesulfonate (Mesylate)

In 100 ml methylene chloride was dissolved 10.4 gm (17.8 mmol) of DMT-protected HEO from Example 1A above. The solution was ice cooled and 4.59 gm (35.6 mmol) of diisopropylethylamine was added, followed by the addition of 2.06 g (26.7 mmol) methanesulfonyl chloride. The reaction mixture was stirred for 30 minutes and then washed with a saturated solution of NaHCO$_3$, brine and dried over Na$_2$SO$_4$. The solvent was removed in vacuo to give 11.93 gm of the mesylate (compound 3 in FIG. 2).

D. DMT-Protected HEO Dimer

To a suspension of 0.62 gm (26.9 mmol) of sodium hydride in 150 ml freshly distilled tetrahydrofuran at 10° C. was added 10.14 gm (36.0 mmol) of hexaethylene glycol over 1 minute, and the mixture was stirred at room temperature for 30 minutes. To this was added a solution of 11.93 gm (17.9 mmol) of HEO mesylate from Example 1C above in 50 ml tetrahydrofuran. The reaction mixture was warmed to 40°–50° C. for 3 hours, after which the solvent was removed in vacuo and the residue was brought up in 150 ml of methylene chloride. This was washed with 3×100 ml H$_2$O, brine and dried over Na$_2$SO$_4$. The solvent was removed in vacuo to give a crude oil (13.37 gm), which was purified by silica gel chromatography as in Example 1A above. 10.0 gm of the DMT-protected HEO dimer (11.8 mmol) was recovered. Analysis of the material (compound 4 in FIG. 2) showed:

$^1$HNMR (300 MHz CDCl$_3$) δ7.5–6.8 (mult., 13H aromatic), 3.75 (S, 6H, OCH$_3$), 3.6 (20H, mult., OCH$_2$—CH$_2$O), 3.5 (2H, mult., CH$_2$—OH), 3.2 (2H, t, CH$_2$ODMT).

E. Phosphoramidite of the DMT-protected HEO dimer (Compound 5 in FIG. 2)

1 gm (1.17 mmol) of DMT-protected HEO dimer from Example 1D and 20 mg (0.12 mmol) of tetrazole diisopropyl ammonium salt were dissolved in 10 ml methylene chloride under inert atmosphere. To this at room temperature was added 0.409 gm (1.35 mmol) of 2-cyanoethyl tetraisopropyl phosphordiamidite. After 15 hr., the reaction was washed with saturated NaHCO$_3$, brine and dried over Na$_2$SO$_4$. The solvent was removed in vacuo to give crude oil (1.44 gm), which was purified by flash chromatography as in Example 1B. 0.76 gm (0.73 mmol) of purified product was recovered. Analysis of the purified material (compound 5 in FIG. 2) showed:

$^{31}$P-NMR (CD$_3$CN, H decoupled): δ151 (s).

Example 2

Synthesis of (HEO)$_N$ Chains Linked By Bisurethane Tolyl Groups

Figure 3:
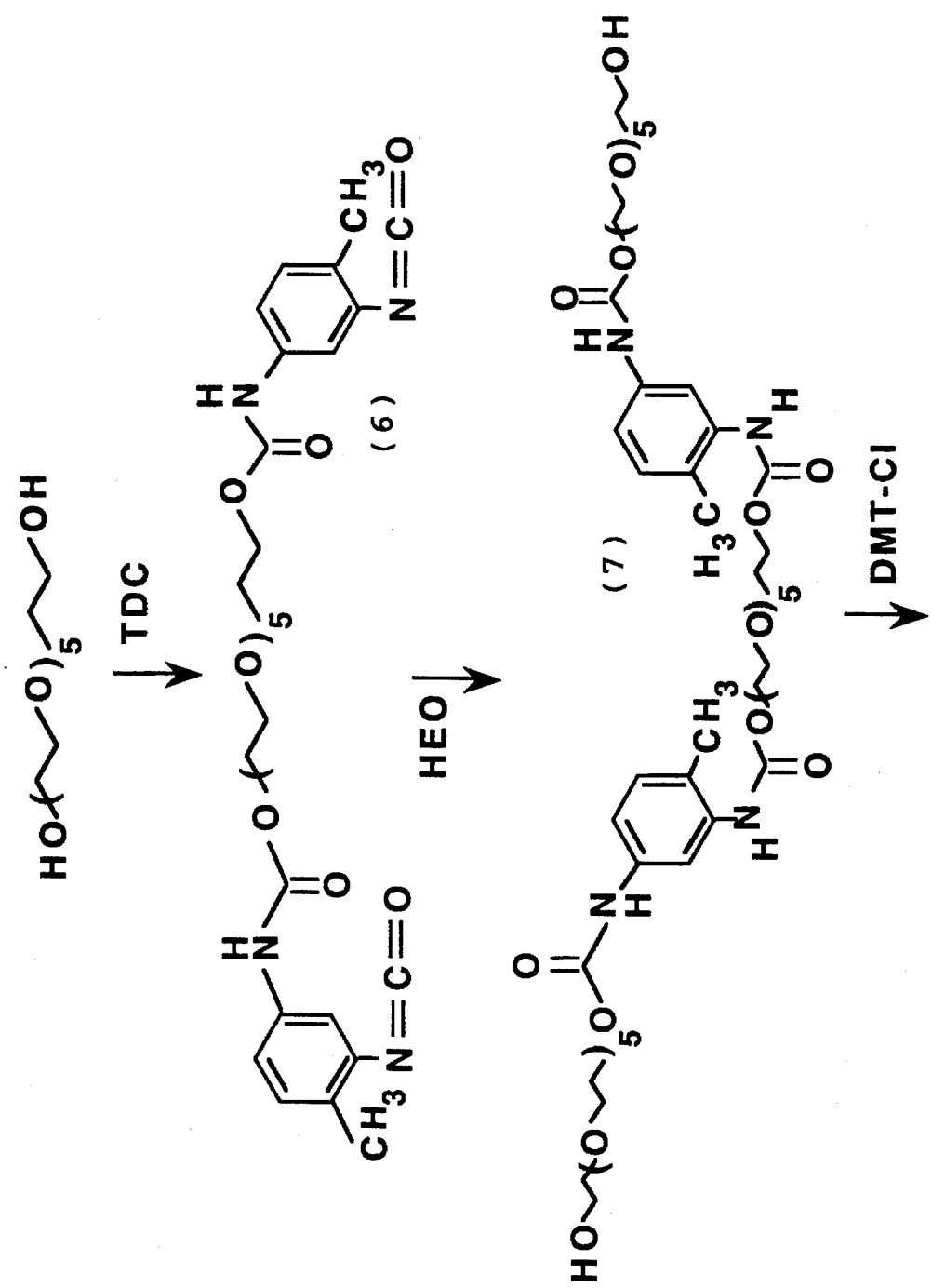
FIG. 3 illustrates methods of synthesis of polyethylene glycol polymer chains in which HEO units are linked by bisurethane tolyl linkages.

The reactions described in this Example are illustrated in FIG. 3.

Hexaethylene glycol (10.0 ml) was added dropwise to tolylene-2,4-diisocyanate (TDC) (17.0 ml) under argon at 30°–35° C. An ice bath was used to control the exothermic reaction. The reaction was allowed to stand at room temperature overnight; washed with hot hexane (10×) to remove excess diisocyanate; and concentrated under reduced pressure to yield the crude bisisocyanate product (compound 6, FIG. 3) as an amber oil (30 g).

A solution of the above crude bisisocyanate (2.3 g) and hexaethylene glycol (7.0 ml) in dichloromethane (25 ml) was stirred at room temperature for 1 hour and then dibutyltindilaurate (0.1 ml, Aldrich) was added and stirred at room temperature for 22 hours; diluted with dichloromethane and washed with water (4×20 ml); dried (MgSO$_4$); and concentrated under reduced pressure to give the crude diol product (compound 7, FIG. 3) as an amber oil (4.6 g).

A solution of DMT chloride (1.2 g) in dichloromethane (20 ml) was added dropwise over 2 hours under argon at room temperature to a stirred solution of the above crude diol (4.4 g) and triethylamine (0.6 ml, Aldrich) in dichloromethane (25 ml). The reaction solution was stirred at room temperature for 2 hours and washed with water; dried (MgSO$_4$); and concentrated under reduced pressure to give the crude DMT alcohol product as an amber oil (5.1 g). Column chromatography (triethylamine neutralized silica, 5% methanol/dichloromethane) of the crude DMT alcohol gave the purified DMT alcohol (compound 8, FIG. 3) as a viscous amber oil (0.72 g). Analysis of the compound showed: $^1$H NMR/CDCl$_3$: δ6.7–7.5 (m, ArH, 19H), δ4.3 (m, NC(O)OCH2, 8H), δ3.77 (s, CH3O, 6H), δ3.55–3.75 (m, CH2OCH2, 62H), δ3.2 (t, DMTOCH2, 2H), δ2.15 (m, CH3Ar, 6H).

2-Cyanoethyl-N,N,N-,N-tetraisopropylphosphorodiamidite (0.20 ml) was added under argon at room temperature to a stirred solution of the above purified DMT alcohol and tetrazolediisopropylamine salt (12 mg) in dry dichloromethane (5 ml). After stirring at room temperature for 4 hours, NaHCO$_3$ solution was added and stirred for 40 minutes. The dichloromethane layer was diluted with more dichloromethane and washed with brine; dried (MgSO$_4$); and concentrated under reduced pressure to give the crude phosphoramidite product (compound 9, FIG. 3) as an amber oil (0.88 g). $^{31}$P NMR (CDCl$_3$): 151 ppm.

Example 3

Derivatization of Oligonucleotides with PEO Chains

The reactions described in Sections B and C are illustrated in FIGS. 4A and 4B, respectively.

A. Preparation of Oligonucleotide

A 48-base oligonucleotide having the sequence 5'GCAC-CATTAAAGAAAATATCATCTTTGGT-GTTTCCTATGATGAATATA carboxyfluorescein-3' (composition 10 in FIG. 4A) (SEQ ID NO: 1) was prepared using a 3'-linked carboxyfluorescein polystyrene support (Applied Biosystems, Inc.) or can be prepared using 3'-Amine-ON CPG (Clontech, Palo Alto, Calif.) and FAM-NHS (ABI) according to published methods (Applied Biosystems, Caruthers, Connell) and standard phosphoramidite chemistry on an Applied Biosystems 380B DNA Synthesizer.

B. Oligonucleotide Derivatized with PEO Chain

The support-bound oligonucleotide from Example 3A above (0.1 μmol oligonucleotide) was deprotected by reaction with trichloroacetic acid, washed, then reacted with one of the phosphoramidite-PEO polymers as in Example 1, using a standard DNA synthesis cycle. The embodiment shown in FIG. 4A is with polymer chain with 12 ethylene oxide subunits. The derivatized oligonucleotide (Compound 11 in FIG. 4A) was cleaved off the column with trityl on and purified by liquid chromatography, using an ABI RP-300 (C-8) 4.6×220 mm column and a 0.1M triethylammonium acetate-water and acetonitrile solvent system. The collected product was detritylated with acetic acid to give the derivatized oligonucleotide (compound 12 in FIG. 4A).

C. Oligonucleotide derivatized with bisurethane tolyl-linked PEO Chain

The support-bound oligonucleotide from Example 3A above (0.1 μmol oligonucleotide) (Compound 10, FIG. 4B) was reacted with a phosphoramidite-PEO bisurethane tolyl-linked polymer (Compound 9 in FIG. 3) prepared as in Example 2 using a standard DNA synthesis cycle. The derivatized oligonucleotide (Compound 13 in FIG. 4B) was cleaved from the column and deprotected with trityl on, and purified by liquid chromatography, using an ABI RP-300 (C-8) 4.6×220 mm column and a 0.1M triethylammonium acetate-water and acetonitrile solvent system. The collected product was deprotected with acetic acid. The derivatized oligonucleotide is shown as compound 14 in FIG. 4B.

Example 4

Successive PEO Additions to an Oligonucleotide

The reaction steps described in this Example are illustrated in FIG. 5.

A. FAM-Labeled Oligonucleotide

A 24 base oligonucleotide having the sequence 5' TTG GTG TTT CCT ATG ATG AAT ATA-LAN-T3' (SEQ ID NO: 2) was made on an ABI model 380B DNA synthesizer using standard phosphoramidite chemistry (composition 15 in FIG. 5). LAN is a base-modified deoxyuridine phosphoramidite (Molecular Biosystems Inc.) with a TFA-protected amine. The 24-mer was made from a 1 μmol column using trityl on manual protocol after completion of synthesis. The column material was divided into 10 separate 0.1 μmol columns.

All of the subsequent oligos were cleaved off the support with NH$_4$OH and purified first by HPLC using an ABI RP-300 (C-8) column (4.6×220 mm) using a flow rate of 1.5 ml/min. and a solvent gradient of 0.1M triethylammonium acetate-water pH 7.0 and acetonitrile. After the specific modifications described below, the trityl group was removed and the product was isolated by HPLC using the conditions described above.

The cleaved oligonucleotides were labeled with FAM by adding a solution of the amine-labeled 24-mer with 15 μl of FAM•NHS in DMSO (ABI) and 40 μl of 1M NaHCO$_3$/Na$_2$CO$_3$ pH 9.0. After 2 hours the reaction mixtures were passed through a Pharmacia PD-10 Sephadex G25M column (Pharmacia) and the collected samples were then HPLC purified. After removal of the solvent the samples are detritylated with 80% acetic acid-water. The solvent was then removed in vacuo, and the residue was brought up in 0.5 ml H$_2$O and purified by liquid chromatography.

B. FAM Labeled PEO-Derivatized Oligonucleotides

DMT-protected phosphoramidite HEO units from Example 1B were added to the 5' end of the oligo from Example 4A by standard phosphoramidite chemistry on solid support, yielding the composition 16 in FIG. 5. One to four units were added in separate reactions. The resulting HEO-modified oligos were cleaved off the solid support (Compound 17, FIG. 5) as above, and labeled with FAM and purified (Compound 18, FIG. 5), also as described above.

C. PEO-Derivatized Oligonucleotides

A 25 base oligonucleotide having the sequence 5' GGC ACC ATT AAA GAA AAT ATC ATC T 3' (SEQ ID NO: 3) was made as described in Example 4A. DMT-protected phosphoramidite HEO units were added to the 5' end of this 25 mer and purified as described in Example 4B.

Example 5

Addition of —NH(CH$_2$CH$_2$O)$_7$CH$_2$CO— Subunits to an Oligonucleotide

A 25-mer oligonucleotide having the sequence 5' GGC ACC ATT AAA GAA AAT ATC ATC T 3' (SEQ ID NO: 3) was prepared and de-tritylated on a CPG support as described above. The 5'-hydroxyl group of the 25-mer was then derivatized with N—MMT—C$_6$ Amino Modifier (Clontech Laboratories, Palo Alto, Calif.; Compound 20 in FIG. 6) using standard phosphoramidite chemistry. The monomethoxytrityl group was removed using a standard trityl cleavage protocol on an ABI DNA synthesizer (yielding Compound 21 in FIG. 6.), and the DNA synthesis column was then transferred to an ABI Peptide synthesizer capable of performing FMOC chemistry.

Using standard FMOC peptide synthesis protocols, one or more monomers of H$_2$N(CH$_2$CH$_2$O)$_7$CH$_2$CO$_2$H (HAA units) were added sequentially to the 5'-terminal amine of compound 21 by the procedure described below. After completion of the synthesis, the terminal amine of the resultant peptide was acetylated with acetic anhydride using a standard peptide capping protocol, yielding the derivatized oligonucleotides represented at formula 24 in FIG. 6.

A more specific procedure for the addition of HAA units is as follows. In a 1.5 ml Eppendorf tube was placed 50 mg (82 μmole) of FMOC—NH(CH$_2$CH$_2$O)$_7$CH$_2$CO$_2$H, 375 μl of 0.4M diisopropylethylamine (DIPEA) in DMF, and 375 μl of 0.2M hydroxybenzotriazole uronium salt (HBTU) in hydroxybenzotriazole (HOBT). The immobilized N—MMT—C$_6$-derivatized oligonucleotide from above was detritylated in an ABI 394 Synthesizer column by reaction with trichloroacetic acid (TCA) for 3 minutes. The detritylated product (Compound 21 in FIG. 6) was washed with CH$_3$CN for 1 minute and then dried with argon.

The following steps were then used to produce oligonucleotide species derivatized with 1, 2, 3, or 4 HAA units (compound 24 in FIG. 6; n=1, 2, 3, or 4).

(1) The solution of FMOC—NH(CH$_2$CH$_2$O)$_7$CH$_2$CO$_2$H prepared in the Eppendorf tube as above was loaded in a syringe and passed back and forth through the immobilized oligonucleotide (Compound 21) for 10 minutes, thereby forming a new oligonucleotide derivative containing one HAA unit (Compound 23, n=1).

(2) This derivative was washed with 5 mL of DMF, and then with 5×1 ml aliquots of 20% piperidine in DMF to cleave the FMOC group from the terminal amine. The reaction was monitored by following the decrease in absorbence (300 nm) in each successive wash step. The column was then rinsed with 20 ml DMF.

(3) For adding additional HAA units to the oligonucleotide derivative, steps 1 and 2 were repeated until the desired number of HAA units was achieved.

(4) The product was capped with acetic anhydride (Ac$_2$O) and released from the solid support by standard procedures, yielding Compound 24.

Example 6

Reversed Phase Chromatographic Separation of Probes

A crude mixture of the 25-mer of Example 5 derivatized with 0, 1, 2, 3 and 4 HAA units (Compound 24 in FIG. 6) was resolved using a Perkin Elmer Series 410 HPLC system equipped with an ABI RP-300 reversed phase column (4.6× 220 mm, 7 μm, 300 Å pore size). A linear gradient of 10–25% acetonitrile in 0.1M triethylammonium acetate pH 7.0 over 30 minutes was used, with a flow rate of 1.5 mL/min. The resultant chromatogram is shown in FIG. 7.

Example 7

Conjugation of a Peptide to an Oligonucleotide

A 25-mer oligonucleotide was synthesized on CPG solid support with an ABI DNA synthesizer. To the 5' hydroxyl of the CPG-supported oligonucleotide was added N—MMT—C$_6$ Amino Modifier using standard phosphoramidite chemistry. N—MMT—C$_6$ Amino Modifier is a monomethoxytrityl-protected amino linked phosphoramidite which is commercially available from Clontech Laboratories, Palo Alto, Calif. The monomethoxytrityl group was removed using a standard trityl cleavage protocol on a DNA synthesizer and the DNA synthesis column was then placed on an ABI Peptide synthesizer capable of performing FMOC chemistry. Using standard FMOC peptide synthesis protocols, a four and an eight unit amino acid peptide was conjugated onto the 5'-terminal amine of the CPG supported oligonucleotide. After completion of the synthesis, the terminal amine of the peptide was acetylated using a standard peptide capping protocol.

The synthesis column was then placed onto an ABI DNA synthesizer and the peptide-oligonucleotide was cleaved off the support and purified by HPLC using the conditions as previously described to produce the peptide-oligonucleotides Ac-(Phe-Ala)$_{2 \text{ or } 4}$—NH(CH$_2$)$_6$ -phosphate 5' GGC ACC ATT AAA GAA-AAT ATC ATC T-3' (SEQ ID NO: 3). Ligation of the peptide-oligonucleotide to a fluorescent-labeled oligonucleotide in the presence of an oligonucleotide target was performed as described in Example 8.

Example 8

Ligation of Probe Elements

A first probe having the sequence 5' GGC ACC ATT AAA GAA AAT ATC ATC T-3' (SEQ ID NO: 3) was derivatized with a either a tetrapeptide Phe-Ala-Phe-Ala (SEQ ID NO: 4), or an octapeptide Phe-Ala-Phe-Ala-Phe-Ala-Phe-Ala (SEQ ID NO: 5) according to methods in Example 7. A second probe having the sequence 5' P-TTG GTG TTT CCT ATG ATG AAT ATA G JOE 3' (SEQ ID NO: 6) was prepared with 3-amine-ON CPG, and 5'-phosphate-ON, both from Clonetech (Palo Alto, Calif.), and with JOE-NHS (Applied Biosystems, Inc.) using published methods (Applied Biosystems Bulletin; Aruthers; Connell).

The probes were targeted against a 48-base oligonucleotide (SEQ ID NO: 1) representing the F508 region of the cystic fibrosis gene. Probe hybridization to the target and ligation of the hybridized probes was performed substantially as follows:

Peptide-derivatized oligonucleotide (50 nM, 20 μl), and the fluorescence-labeled oligonucleotide (50 nM, 20 μl) were mixed with target oligonucleotide (50 nM, 20 μl); salmon sperm DNA (4 ug/10 μl, 20 μl); 10× reaction buffer (200 mM Tris•HCl pH 7.6; 1M KCl; 100 mM MgCl$_2$; 100 mM dithiothreitol; 10 mM nicotinamideadeninedinucleotide) (20 μl); ligase (30 units, 100 units/μl, Epicentre Technologies Ampligase, Madison, Wis.) and 100 μl of distilled water. The prepared sample was overlayed with 50 ul of oil and heated in a Perkin-Elmer Cetus DNA Thermal Cycler (Norwalk, Conn.) at 94° C. for 3 minutes and then at 62° C. for 60 minutes.

Example 9

LCR Amplification of Ligated Probes

The following four probes were prepared:

(1) 5' GGC ACC ATT AAA GAA AAT ATC ATC T-3' (SEQ ID NO: 3) derivatized at its 5' end with a either a 2 or 4 unit DEO (dodeca-(ethylene oxide)) polymer chains, according to synthetic methods described in Example 4, except in this case the units are 12-mers (2 or 4 12-mers) of ethylene oxide;

(2) 5' P-TTG GTG TTT CCT ATG ATG AAT ATA G 3'-JOE• (SEQ ID NO: 6), prepared as in Example 8; (3) 5' ROX-CTA TAT TCA TCA TAG GAA ACA CCA AA 3'—OH• (SEQ ID NO: 7), prepared according to published methods (Applied Biosystems); and (4) 5'—P— GAT GAT ATT TTC TTT AAT GGT GCC-3' TAMRA• (SEQ ID NO: 8) prepared with 3'-Amine-ON CPG, 5'-Phosphate-ON and Tamra-NHS (ABI) using published methods (Applied Biosystems, Caruthers, Connell).

Probes 1 and 2 are designed to span a portion of one strand of the F508 region of the cystic fibrosis gene, as in Example 8. Probes 3 and 4 are designed to span the same portion of the F508 region of the opposite strand of the gene. Ligase chain reaction was performed according to published methods (Winn-Deen). Briefly, LCR assays were carried out in 20 mmol/L Tris•HCl buffer, pH 7.6, containing 100 mmol of K$^+$, 10 mmol of Mg$^{2+}$, 10 mmol of dithiothreitol, 1 mL of Triton X-100, and 1 mmol of AND$^+$ per liter. Each 100 µL of reaction mixture contained 1 pmol of each of the four oligonucleotides and 15 U of thermal-stable ligase (Epicentre Technologies, Madison, Wis.). To mimic the complexity of the human genome, we added 4 µg of herring sperm DNA to each reaction mixture. Reactions were carried out in 100 µL aliquots overlayed with 100 µL of mineral oil in Thin Walled Gene-Amp™ (Perkin-Elmer Cetus, Norwalk, Conn.) reaction tubes. All LCR reactions were run in a Perkin-Elmer Cetus model 9600 thermal cycler for 30 cycles of 94° C. (10S) and 60° C. (2 min). At the end of the cycling protocol, the reactions were cooled to 4° C.

Although the invention has been described with reference to various applications, methods, and compositions, it will be appreciated that various changes and modification may be made without departing from the invention.

It is claimed:

1. A method of detecting the presence or absence of a plurality of selected target sequences in a target polynucleotide, comprising
adding to a target polynucleotide, a plurality of different-sequence probe pairs, where each probe pair includes two polynucleotide probe elements which are complementary in sequence to adjacent portions of a selected one of the target sequences in the target polynucleotide, and one of the elements in each probe pair contains a nonpolynucleotide polymer chain which imparts a distinctive electrophoretic mobility in a sieving matrix, to the associated probe pair, when the elements in the pair are ligated,
hybridizing the probe pairs with the target polynucleotide,
treating the hybridized polynucleotides under conditions effective to ligate the end subunits of target-bound probe elements when their end subunits are base-paired with adjacent target bases,
releasing the ligated probe pairs from the target polynucleotide,
separating the released, ligated probe pairs by electrophoresis in such a sieving matrix,
and detecting the ligated probe pairs formed, to determine the presence or absence of the selected target sequences.

2. The method of claim 1, wherein said polynucleotide probe elements have substantially the same lengths, as evidenced by the ability of said polynucleotide probe elements to hybridize to their associated target sequences with the same hybridization reaction kinetics.

3. The method of claim 1, wherein prior to said releasing, said ligated probe pairs are amplified by repeated cycles of probe binding and ligation.

4. The method of claim 1, wherein the second probe element in each probe includes two alternative-sequence oligonucleotides which (i) are complementary to alternative sequences in the same portion of an associated target sequence and (ii) are derivatized with different detectable reporters, and said detecting includes determining a mutation state of each said target sequence according to (a) a signature electrophoretic mobility of each probe, which identifies the target sequence associated with that probe, and (b) a signature reporter label, which identifies the mutation state of that target sequence.

5. The method of claim 1, wherein the first probe element in each probe includes two alternative-sequence oligonucleotides which (i) are complementary to alternative sequences in the same portion of an associated target sequence and (ii) are derivatized with different nonpolynucleotide polymer chains which impart a distinctive electrophoretic mobility to each associated probe pair, when the elements in the pair are ligated, and said detecting includes determining a mutation state of each said target sequence according to (a) a signature reporter label which identifies the target sequence associated with that probe, and (b) a signature electrophoretic mobility, which identifies the mutation state of that target sequence.

6. The method of claim 1, wherein said nonpolynucleotide polymer is selected from the group consisting of polyethylene oxide, polyglycolic acid, polylactic acid, polypeptide, oligosaccharide, polyurethane, polyamide, polysulfonamide, polysulfoxide, polyphosphonate, and block copolymers thereof, including polymers composed of units of multiple subunits linked by charged or uncharged linking groups.

7. The method of claim 1, wherein said hybridizing is carried out with the target polynucleotide immobilized on a solid support; and prior to said releasing, the immobilized target polynucleotide is washed to remove probe pairs not bound to the target polynucleotide in a sequence-specific manner.

8. A method of detecting the presence or absence of a plurality of selected target sequences in a target polynucleotide, comprising adding to a target polynucleotide, a plurality of different-sequence probe pairs, where each probe pair includes two polynucleotide probe elements which are complementary in sequence to adjacent portions of a selected one of the target sequences in the target polynucleotide, and one of the elements in each probe pair contains a nonpolynucleotide polymer chain which imparts a distinctive elution characteristic in a chromatographic separation medium to the associated probe pair, when the elements in the pair are ligated, hybridizing the probe pairs with the target polynucleotide, treating the hybridized polynucleotides under conditions effective to ligate the end subunits of target-bound probe elements when their end subunits are base-paired with adjacent target bases, releasing the ligated probe pairs from the target polynucleotide, separating the released, ligated probe pairs by chromatography in such a chromatographic separation medium, and detecting the ligated probe pairs formed, to determine the presence or absence of the selected target sequences.

9. The method of claim 8, wherein said polynucleotide probe elements have substantially the same lengths, as evidenced by the ability of said polynucleotide probe elements to hybridize to their associated target sequences with the same hybridization reaction kinetics.

10. The method of claim 8, wherein prior to said releasing, said ligated probe pairs are amplified by repeated cycles of probe binding and ligation.

11. The method of claim 8, wherein the second probe element in each probe includes two alternative-sequence oligonucleotides which (i) are complementary to alternative sequences in the same portion of an associated target sequence and (ii) are derivatized with different detectable reporters, and said detecting includes determining a mutation state of each said target sequence according to (a) a signature elution characteristic of each probe, which identifies the target sequence associated with that probe, and (b) a signature reporter label, which identifies the mutation state of that target sequence.

12. The method of claim 8, wherein the first probe element in each probe includes two alternative-sequence oligonucleotides which (i) are complementary to alternative sequences in the same portion of an associated target sequence and (ii) are derivatized with different nonpolynucleotide polymer chains which impart a distinctive electrophoretic mobility to each associated probe pair, when the elements in the pair are ligated, and said detecting includes determining a mutation state of each said target sequence according to (a) a signature reporter label of each probe, which identifies the target sequence associated with that probe, and (b) a signature elution characteristic, which identifies a mutation state of that target sequence.

13. The method of claim 8, wherein said nonpolynucleotide polymer is selected from the group consisting of polyethylene oxide, polyglycolic acid, polylactic acid, polypeptide, oligosaccharide, polyurethane, polyamide, polysulfonamide, polysulfoxide, polyphosphonate, and block copolymers thereof, including polymers composed of units of multiple subunits linked by charged or uncharged linking groups.

14. The method of claim 8, wherein said hybridizing is carried out with the target polynucleotide immobilized on a solid support; and prior to said releasing, the immobilized target polynucleotide is washed to remove probe pairs not bound to the target polynucleotide in a sequence-specific manner.

15. A method of detecting the presence or absence of a plurality of selected target sequences in a target polynucleotide, comprising adding to the target polynucleotide, a plurality of sequence-specific probes, each comprising an oligonucleotide-binding polymer having a probe-specific sequence of subunits designed for base-specific binding of the binding polymer to a target sequence, and attached to the binding polymer, a nonpolynucleotide polymer chain which imparts to the probe a distinctive electrophoretic mobility in a sieving matrix, reacting the probes with the target polynucleotide under conditions favoring binding of the probes in a base-specific manner to the target polynucleotide, treating the probes to selectively modify those probes which have bound to the target polynucleotide in a sequence-specific manner, to form modified, labeled probes, each having a detectable reporter label and a distinctive electrophoretic mobility in a sieving matrix, fractionating the modified, labeled probe(s) by electrophoresis in a sieving matrix, and detecting the modified, labeled probe(s) to determine the presence or absence of the selected target sequences.

16. The method of claim 15, wherein the different-sequence binding polymers have substantially the same lengths.

17. The method of claim 15, wherein (i) each sequence-specific probe includes first and second probe elements having first and second oligonucleotide probe elements effective to bind to adjacent regions of a target sequence, (ii) one of the elements in each probe is derivatized with said polymer chain, (iii) said reacting is effective to bind both oligonucleotides to their specific target sequences, and (iv) said treating includes ligating the oligonucleotides bound to the target polynucleotide under conditions effective to ligate the end subunits of target-bound oligonucleotides when their end subunits are base-paired with adjacent target bases, to form ligated probes, and releasing the ligated probe from the target polynucleotide.

18. The method of claim 17, wherein the first probe element is reporter-labeled.

19. The method of claim 17, wherein the second probe element is reporter-labeled.

20. The method of claim 17, wherein said treating further includes subjecting the ligated probe to repeated cycles of probe binding and ligation, to amplify the concentration of ligated probe.

21. The method of claim 17, wherein said treating further includes subjecting each ligated probe to repeated cycles of probe binding and ligation in the presence of a second pair of probe elements having oligonucleotides which together have a sequence which is complementary to the selected ligated probe, to amplify the ligated probe in an exponential manner.

22. The method of claim 17, wherein said second probe element in each probe pair includes two alternative-sequence oligonucleotides which (i) are complementary to alternative sequences in the same portion of an associated target sequence and (ii) are derivatized with different detectable reporters, and said detecting includes determining a mutation state of each said target sequence according to (a) a signature electrophoretic migration rate of each probe, which identifies the target sequence associated with that probe, and (b) a signature reporter label, which identifies the mutation state of that target sequence.

23. The method of claim 15, wherein (i) each sequence-specific probe includes first and second primer elements having first and second sequence-specific oligonucleotides effective to hybridize with opposite end regions of complementary strands of a target polynucleotide, where the oligonucleotide in the first primer element is derivatized with a probe-specific polymer chain, (ii) said reacting is effective to bind both primer oligonucleotides to opposite end regions on complementary strands of the target polynucleotide, and (iii) said treating is effective to amplify the target polynucleotide by primer-initiated polymerase chain reaction.

24. The method of claim 23, wherein the oligonucleotide in the second primer element is reporter-labeled, and the labeled probes are double stranded polynucleotide fragments.

25. The method of claim 23, wherein said treating further includes hybridizing to the amplified target sequences, with such in single-stranded form, single-stranded reporter-labeled oligonucleotides whose sequences are complementary to regions of the amplified target sequences, to form labeled probes.

26. The method of claim 15, wherein each sequence-specific probe includes a binding polymer and an attached reporter label, and said treating includes reacting the hybridized probes and target with DNA polymerase in the presence of a reporter-labeled nucleoside triphosphate molecule, to form said labeled probes.

27. The method of claim 15, wherein each sequence-specific probe includes a binding polymer composed of a first single-stranded DNA segment, and a second segment which includes single-stranded RNA, where the polymer chain is attached to said first segment and a reporter is attached to said second segment, and said treating includes reacting hybridized probe with an RNase enzyme specific for RNA/DNA substrate, to form modified, labeled probe lacking the polymer chain.

28. The method of claim 15, wherein each sequence-specific probe includes a binding polymer composed of a first single-stranded DNA segment, and a second segment which includes single-stranded RNA, the polymer chain and reporter label are attached to said first segment, and said treating includes reacting hybridized probe with an RNAse enzyme specific for RNA/DNA substrate, to form modified, labeled probe lacking said second binding polymer segment.

29. The method of claim 15, wherein each sequence-specific probe includes an oligonucleotide binding polymer having a 5'-end, said polymer chain and a reporter label are attached to an oligonucleotide subunit adjacent said 5'-end, and said treating includes enzymatically cleaving said adjacent subunit from the binding polymer.

30. The method of claim 15, wherein each sequence-specific probe includes a binding polymer and an attached reporter label, and said treating includes immobilizing said target polynucleotide, washing the immobilized target polynucleotide to remove probes not bound to the target polynucleotide in a sequence-specific manner, and denaturing the target polynucleotide to release probes bound in a sequence-specific manner.

31. A method of detecting the presence or absence of a plurality of selected target sequences in a target polynucleotide, comprising adding to the target polynucleotide, a plurality of sequence-specific probes, each comprising an oligonucleotide-binding polymer having a probe-specific sequence of subunits designed for base-specific binding of the binding polymer to a target sequence, and attached to the binding polymer, a nonpolynucleotide polymer chain which imparts to the probe a distinctive elution characteristic in a chromatographic separation medium, reacting the probes with the target polynucleotide under conditions favoring binding of the probes in a base-specific manner to the target polynucleotide, treating the probes to selectively modify those probes which have bound to the target polynucleotide in a sequence-specific manner, to form modified, labeled probes, each having a detectable reporter label and a distinctive elution characteristic in a chromatographic separation medium, fractionating the modified, labeled probe(s) by chromatography in a chromatographic medium, and detecting the modified, labeled probe(s) to determine the presence or absence of the selected target sequences.

32. The method of claim 31, wherein the different-sequence binding polymers have substantially the same lengths.

33. The method of claim 31, wherein (i) each sequence-specific probe includes first and second probe elements having first and second oligonucleotide probe elements effective to bind to adjacent regions of a target sequence, (ii) one of the elements in each probe is derivatized with said polymer chain, (iii) said reacting is effective to bind both oligonucleotides to their specific target sequences, and (iv) said treating includes ligating the oligonucleotides bound to the target polynucleotide under conditions effective to ligate the end subunits of target-bound oligonucleotides when their end subunits are base-paired with adjacent target bases, to form ligated probes, and releasing the ligated probe from the target polynucleotide.

34. The method of claim 33, wherein the first probe element is reporter-labeled.

35. The method of claim 33, wherein the second probe element is reporter-labeled.

36. The method of claim 33, wherein said treating further includes subjecting the ligated probe to repeated cycles of probe binding and ligation, to amplify the concentration of ligated probe.

37. The method of claim 33, wherein said treating further includes subjecting each ligated probe to repeated cycles of probe binding and ligation in the presence of a second pair of probe elements having oligonucleotides which together have a sequence which is complementary to the selected ligated probe, to amplify the ligated probe in an exponential manner.

38. The method of claim 33, wherein said second probe element in each probe pair includes two alternative-sequence oligonucleotides which (i) are complementary to alternative sequences in the same portion of an associated target sequence and (ii) are derivatized with different detectable reporters, and said detecting includes determining a mutation stage of each said target sequence according to (a) a signature chromatographic elution characteristic of each probe, which identifies the target sequence associated with that probe, and (b) a signature reporter label, which identifies the mutation state of that target sequence.

39. The method of claim 31, wherein (i) each sequence-specific probe includes first and second primer elements having first and second sequence-specific oligonucleotides effective to hybridize with opposite end regions of complementary strands of a target polynucleotide, where the oligonucleotide in the first primer element is derivatized with a probe-specific polymer chain, (ii) said reacting is effective to bind both primer oligonucleotides to opposite end regions on complementary strands of the target polynucleotide, and (iii) said treating is effective to amplify the target polynucleotide by primer-initiated polymerase chain reaction.

40. The method of claim 39, wherein the oligonucleotide in the second primer element is reporter-labeled, and the labeled probes are double stranded polynucleotide fragments.

41. The method of claim 39, wherein said treating further includes hybridizing to the amplified target sequences, with such in single-stranded form, single-stranded reporter-labeled oligonucleotides whose sequences are complementary to regions of the amplified target sequences, to form labeled probes.

42. The method of claim 31, wherein each sequence-specific probe includes a binding polymer and an attached reporter label, and said treating includes reacting the hybridized probes and target with DNA polymerase in the presence of a reporter-labeled nucleoside triphosphate molecule, to form said labeled probes.

43. The method of claim 31, wherein each sequence-specific probe includes a binding polymer composed of a first single-stranded DNA segment, and a second segment which includes single-stranded RNA, where the polymer chain is attached to said first segment and a reporter is attached to said second segment, and said treating includes reacting hybridized probe with an RNase enzyme specific for RNA/DNA substrate, to form modified, labeled probe lacking the polymer chain.

44. The method of claim 31, wherein each sequence-specific probe includes a binding polymer composed of a first single-stranded DNA segment, and a second segment which includes single-stranded RNA, the polymer chain and reporter label are attached to said first segment, and said treating includes reacting hybridized probe with an RNase enzyme specific for RNA/DNA substrate, to form modified, labeled probe lacking said second binding polymer segment.

45. The method of claim 31, wherein each sequence-specific probe includes an oligonucleotide binding polymer having a 5'-end, said polymer chain and a reporter label are attached to an oligonucleotide subunit adjacent said 5'-end, and said treating includes enzymatically cleaving said adjacent subunit from the binding polymer.

46. The method of claim 31, wherein each sequence-specific probe includes a binding polymer and an attached reporter label, and said treating includes immobilizing said target polynucleotide, washing the immobilized target polynucleotide to remove probes not bound to the target polynucleotide in a sequence-specific manner, and denaturing the target polynucleotide to release probes bound in a sequence-specific manner.

* * * * *

UNITED STATES PATENT AND TRADEMARK OFFICE
CERTIFICATE OF CORRECTION

PATENT NO. : 5,514,543
DATED : May 7, 1996
INVENTOR(S) : Paul D. Grossman et al.

It is certified that error appears in the above-identified patent and that said Letters Patent is hereby corrected as shown below:

Column 1,
Lines 5-9, delete the contents in their entirety and insert therefor
-- This application is a continuation-in-part of co-owned applications Ser. No. 07/973,118, filed Nov. 6, 1992, abandoned, which is a continuation-in-part of co-owned applications Ser. No. 07/866,018, filed Apr. 7, 1992, and Ser. No. 07/862,642, filed Apr. 3, 1992, abandoned. --

Signed and Sealed this

Second Day of April, 2002

*Attest:*

JAMES E. ROGAN
*Director of the United States Patent and Trademark Office*

*Attesting Officer*